United States Patent
Kurokawa et al.

(10) Patent No.: US 6,226,861 B1
(45) Date of Patent: May 8, 2001

(54) METHOD AND APPARATUS FOR GAS CONCENTRATION DETECTION AND MANUFACTURING METHOD OF THE APPARATUS

(75) Inventors: Eiichi Kurokawa, Okazaki; Satoshi Hada, Kariya; Tomoo Kawase, Nagoya; Toshiyuki Suzuki, Handa; Satoshi Haseda, Okazaki, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/370,896

(22) Filed: Aug. 10, 1999

Related U.S. Application Data

(62) Division of application No. 09/064,155, filed on Apr. 22, 1998, now Pat. No. 5,980,710.

(30) Foreign Application Priority Data

May 21, 1997 (JP) .................................... 9-131366
Mar. 6, 1998 (JP) .................................... 10-055149

(51) Int. Cl.[7] .................................................. H05B 3/00
(52) U.S. Cl. .................................. 29/611; 29/621; 29/593
(58) Field of Search .................................. 29/610.1, 621, 29/611, 593; 73/23.32; 123/440, 489; 204/424, 425, 426

(56) References Cited

U.S. PATENT DOCUMENTS

| | | |
|---|---|---|
| 4,258,563 | 3/1981 | Yasuda et al. . |
| 4,306,444 | 12/1981 | Hattori et al. . |
| 4,328,477 * | 5/1982 | Takami et al. ...................... 29/610.1 |
| 4,472,247 | 9/1984 | Rohr et al. . |
| 4,532,013 | 7/1985 | Dietz et al. . |
| 4,759,827 | 7/1988 | Okada et al. . |
| 4,915,080 | 4/1990 | Nakaniwa et al. . |
| 5,151,166 | 9/1992 | Harral et al. . |
| 5,182,136 * | 1/1993 | Saburi ................................ 29/610.1 |
| 5,810,997 | 9/1998 | Okazaki et al. . |

FOREIGN PATENT DOCUMENTS

| | | |
|---|---|---|
| 2290620 | 1/1996 | (GB) . |
| 61-237047 | 10/1986 | (JP) . |
| 61-280560 | 12/1986 | (JP) . |

* cited by examiner

*Primary Examiner*—Lee Young
*Assistant Examiner*—Sean Smith
(74) *Attorney, Agent, or Firm*—Nixon & Vanderhye P.C.

(57) ABSTRACT

An A/F sensor generates a current signal corresponding to an air-fuel ratio in response to a voltage applied by a bias control circuit. After a sensor current is received as a voltage signal via a voltage follower, it is outputted to an A/D converter having a predetermined input voltage range, 0 to 5V. A sensor current detection circuit has a plurality of current detection resistors. In order to variably set the resistance value by the sensor current detection circuit, a switch circuit is switched in accordance with the sensor current depending on whether the A/F value to be detected is in the zone near the stoichiometric ratio or in other air-fuel ratio zones.

9 Claims, 16 Drawing Sheets

METHOD AND APPARATUS FOR GAS CONCENTRATION DETECTION AND MANUFACTURING METHOD OF THE APPARATUS

RELATED APPLICATION

This application is a division of our prior application Ser. No. 09/064,155 filed Apr. 22, 1998, now issued as U.S. Pat. No. 5,980,710.

CROSS REFERENCE TO RELATED APPLICATION

This application relates to and incorporates herein by reference Japanese Patent Applications No. 9-131366 filed on May 21, 1997 and No. 10-55149 filed on Mar. 6, 1998.

BACKGROUND OF THE INVENTION

1. Field of the Invention

The present invention relates to a gas concentration detecting apparatus and method and a manufacturing method for the apparatus. The apparatus and method uses a gas concentration sensor for outputting a current signal corresponding to a gas concentration of gas to be detected when a voltage is applied. The apparatus and method is, for example, embodied in a gas concentration detecting apparatus applied to a gas concentration feedback control system of an engine employed in a vehicle.

2. Related Art

For application to a vehicle, a gas concentration detecting apparatus using a gas concentration sensor is proposed. As one example, an air-fuel ratio detecting apparatus using an air-fuel ratio sensor is known.

In an air-fuel ratio control of an engine mounted on a vehicle in recent years, for example, there is a demand for improved control accuracy and a demand for a transition to lean-burn. In order to respond to these demands, a linear air-fuel ratio sensor for detecting the air-fuel ratio of air-fuel mixture supplied to the engine (concentration of oxygen in exhausted gas) linearly over a wide zone and an air-fuel ratio detecting apparatus using the sensor are implemented. As such an air-fuel ratio sensor, for example, in an air-fuel ratio sensor of a limit current type, the zone for detecting a limit current is shifted in accordance with the air-fuel ratio (concentration of oxygen) at that time as is generally known.

The air-fuel ratio sensor of a limit current type has output characteristics in which the farther the air-fuel ratio moves to the lean zone, the more the zone for detecting a limit-current is shifted to the positive-voltage side. The farther the air-fuel ratio moves to the rich side, the more the zone for detecting a limit current is shifted to the negative-voltage side. Consequently, if the applied voltage is held set at a fixed value when the air-fuel ratio changes, it would be impossible to detect an air-fuel ratio accurately by using the zone for detecting a limit current. In a conventional air-fuel ratio detecting apparatus, therefore, the voltage applied to the sensor is varied in accordance with the air-fuel ratio at each time, that is, the sensor current (for example, Japanese Patent Laid-Open Nos. Sho-61-237047 and Sho-61-280560). In this case, the applied voltage is controlled on the basis of an application voltage characteristic line Lx in FIG. 3. By controlling the applied voltage in this way, a desired sensor current (limit current) can be always detected.

The circuit construction of an air-fuel ratio detecting apparatus which is conventionally, implemented is generally shown in FIG. 22. In the diagram, a reference voltage Va generated by a reference voltage circuit 84 is applied to one terminal 82 of an air-fuel ratio sensor 81 and an instruction voltage Vb outputted from a D/A converter 87 is applied to the other terminal 83. The instruction voltage Vb is variably controlled by a CPU (not shown) in accordance with an air-fuel ratio at each time. The circuit construction will be briefly described. The predetermined reference voltage Va generated by the reference ID voltage circuit 84 is amplified by an amplification circuit 85. The same voltage Va as the reference voltage Va from the reference voltage circuit 84 is applied to one terminal 82 of the air-fuel ratio sensor 81. The instruction voltage Vb outputted form the D/A converter 87 is amplified by an amplification circuit 86. The same voltage Vb as the instruction voltage Vb is applied to the other terminal 83 of the air-fuel ratio sensor 81.

The linear type air-fuel ratio sensor 81 conducts a sensor current according to the air-fuel ratio. An A/F output indicative of an air-fuel ratio is therefore detected as an electromotive voltage Vc of a current detection resistor 88 for detecting the sensor current (air-fuel ratio), not a sensor terminal voltage as the predetermined reference voltage Va. In this case, the electromotive voltage Vc is outputted via a voltage follower 89. FIG. 23 is a graph showing a characteristic of an output voltage (A/F value) of each air-fuel ratio. According to the diagram, when the air-fuel ratio is shifted to the lean side, the electromotive voltage Vc is shifted to the positive side with respect to the reference voltage Va. When the air-fuel ratio is shifted to the rich side, the electromotive voltage Vc is shifted to the negative side with respect to the reference voltage Va. A Vc signal (A/F value) obtained in this manner is transmitted from the voltage follower 89 to an A/D converter 90. After A/D-converted by the A/D converter 90, the resultant signal is used for the air-fuel ratio F/B control in a CPU 91 for engine control.

In the air-fuel ratio detecting apparatus having the above configuration, the input voltage range of the A/D converter 90 for receiving the voltage signal (A/F value) is limited to a predetermined range of, for example, "0 to 5V". For instance, in case of using an 8-bit A/D converter, the input voltage range of "0 to 5V" is divided into 256 and the A/F value is read. Specifically, when the air-fuel ratio detection range is set to a zone (A/F=12 to 18) near the stoichiometric ratio in order to perform a stoichiometric control in which the stoichiometric ratio (A/F=14.7) is used as a target air-fuel ratio, the electromotive voltage Vc is outputted in the range of "0 to 5V" by using the current detection resistor 88 in FIG. 22. In this instance, the voltage value per unit A/F (every "1" of the interval of A/F) is "0.833V" and the A/F value is divided into 42 per unit A/F and detected.

On the contrary, for example, in a case where the air-fuel ratio detection range is expanded to A/F=12 to 25 in order to realize lean-burn control, when the air-fuel ratio detecting range is kept set to a range of "0 to 5V", the voltage value per unit A/F is "0.384V" and the A/F value is detected by being divided into 19 per unit A/F. That is, it denotes that the detection accuracy of the air-fuel ratio at the time of the lean-burn control is lower than the detection accuracy of the air-fuel ratio at the time of the stoichiometric control (the higher the voltage value per unit A/F is, the higher the detection accuracy of the air-fuel ratio is). As a result, for example, in the air-fuel ratio control system in which both of the stoichiometric control and the lean-burn control are executed, a problem is caused such that the detection accuracy of the air-fuel ratio near the stoichiometric ratio deteriorates in order to assure the detection accuracy of the air-fuel ratio at the time of lean-burn control.

It is to be noted that the problem of degradation in detection accuracy of the sensor occurs not only in the air-fuel ratio detecting apparatus but also in all of gas concentration detecting apparatuses which use a gas concentration sensor for producing a current signal in accordance with the gas concentration to be detected and are constructed to detect gas concentration from a detection result of the sensor.

SUMMARY OF THE INVENTION

It is an object of the present invention to provide a gas concentration detecting apparatus and method in which the detection accuracy of gas concentration can be improved even when gas concentration detection over a wide range is required.

It is another object of the present invention to provide a manufacturing method for gas concentration detecting apparatus by which gas concentration detection output characteristics can be adjusted.

According to one aspect of the present invention, the resistance value of a current detection resistor is set variably so that gas concentration can be always detected in a voltage range which is readable by a signal processor. For example, The voltage range is "0 to 5V". At this time, it is made possible to assure the highest accuracy within a limitation that the gas concentration is detected within the voltage range. That is, in whatever zones a detected value (sensor current) of a gas concentration sensor resides, the detection accuracy can be assured.

According to another aspect of the present invention, a current detection resistor is provided to produce a plurality of detection signals at different voltage levels, and one of the detection signals is selected in accordance with a current value of a gas concentration sensor.

According to a further aspect of the present invention, a switching condition for switching a resistance value of a current detection resistor is discriminated, and the resistance value is variably set in accordance with a discrimination result of the switching condition.

According to a still further aspect of the present invention, an output voltage of a sensor current detection resistor is monitored, and the output voltage is adjusted by trimming a plurality of voltage dividing resistors which produce a reference voltage to be applied to a gas concentration sensor.

BRIEF DESCRIPTION OF THE DRAWINGS

Other objects, features and advantages of the present invention will be made more apparent from the following detailed description with reference to the accompanying drawings. In the drawings.

DETAILED DESCRIPTION OF THE PREFERRED EMBODIMENT

The present invention will be described hereinbelow with reference to various embodiments which are applied to air-fuel ratio detection in an engine control system.

(First Embodiment)

An air-fuel ratio detecting apparatus in the first embodiment is applied to an air-fuel ratio feedback (F/B) control system of an electronically controlled gasoline injection engine mounted on a vehicle and detects the air-fuel ratio on the basis of components of an exhaust gas exhausted from the engine. An engine control ECU 40 for controlling an air-fuel ratio F/B control selectively executes a stoichiometric control in which the stoichiometric ratio (A/F=14.7) is a target air-fuel ratio and a lean-burn control in which a predetermined lean air-fuel ratio (for example, A/F=22) in a lean zone is a target air-fuel ratio in accordance with an engine operating state.

In the apparatus according to this embodiment, a limit-current type air-fuel ratio sensor (A/F sensor) 30 for outputting a current signal (limit current Ip) corresponding to the air-fuel ratio accompanying application of a voltage Va-Vb is used and the voltage Vp applied to the sensor is controlled by a bias control circuit 10. The limit current Ip detected by the A/F sensor 30 is extracted as a voltage signal and, A/D-converted by an A/D converter (signal processor) 41 having a predetermined input voltage range (0 to 5V in the embodiment), and after that, the resultant data is outputted to a CPU 42 in the engine control ECU. Especially, the apparatus according to this embodiment has a construction such that a resistance value of a current detection resistor 15 provided in the bias control circuit 10 is variably set in order to detect the air-fuel ratio with high accuracy in any air-fuel ratio zone. Specifically, the resistance value of the current detection resistor 15 is properly changed according to the zone near the stoichiometric ratio and other air-fuel ratio zones.

Figure 2:
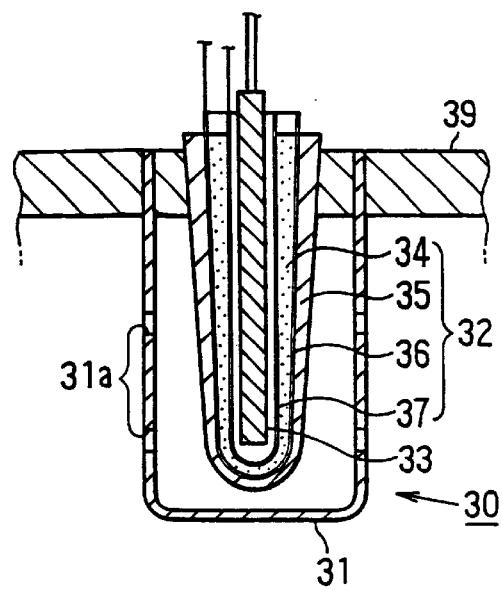
FIG. 2 is a cross sectional view illustrating a construction of an A/F sensor used as a gas concentration sensor.

Referring to FIG. 2, the A/F sensor 30 is installed so as to protrude toward the inside of an engine exhaust pipe 39. Major components of the sensor 30 are a cover 31, a sensor body 32, and a heater 33. The cover 31 has a U-character shape in cross section and a number of small holes 31a are bored through the peripheral wall of the cover 31. The sensor body 32 generates a limit current corresponding to the oxygen-concentration in the lean zone of an air-fuel ratio or the concentration of unburned gas (such as CO, HC, and $H_2$) in the rich zone of the air-fuel ratio.

In the sensor body 32, an exhaust-side electrode layer 36 is firmly attached to the external surface of a solid electrolyte layer 34 formed in a cup shape in cross section and an atmosphere-side electrode layer 37 is firmly attached to the internal surface of the solid electrolyte layer 34. On the outer side of the exhaust-side electrode layer 36, a diffusion resistance layer 35 is formed by a plasma spraying method or the like. The solid electrolyte layer 34 is made of an oxygen ion conducting oxide sintered body which is solid-solved in a material such as $ZrO_2$, $HfO_2$, $ThO_2$, and $Bi_2O_3$ with a material such as CaO, MgO, $Y_2O_3$, and $Yb_2O_3$ used as a stabilizer. The diffusion resistance layer 35 is made of a heat resisting inorganic material such as alumina, magnesia, silica, spinel and mullite. The exhaust-side electrode layer 36 and the atmosphere-side electrode layer 37 are both made of a noble metal with a high catalytic activity such as platinum and have the surfaces to which a porous chemical plating is performed. The area and the thickness of the exhaust-side electrode layer 36 is 10 to 100 $mm^2$ and about 0.5 to 2.0 $\mu$m, respectively. On the other hand, the area and the thickness of the atmosphere-side electrode layer 37 are 10 $mm^2$ or larger and about 0.5 to 2.0 $\mu$m.

The heater 33 is housed in the internal space formed by the atmosphere-side electrode layer 37 and heats the sensor body 32 (atmosphere-side electrode layer 37, the solid electrolyte layer 34, the exhaust-side electrode layer 36, and the diffusion resistance layer 35) by its heat generating energy. The heater 33 has a heat generating capacity sufficient to activate the sensor body 32.

In the A/F sensor 30 having the configuration described above, the sensor body 32 generates a limit current according to the concentration of oxygen in a zone leaner than the stoichiometric ratio point (stoichiometric air-fuel ratio point). In this case, the limit current corresponding to the concentration of oxygen is determined by the area of the exhaust-side electrode layer 36, and the thickness, the porosity and the average pore diameter of the diffusion resistance layer 35. The sensor body 32 is capable of detecting the concentration of oxygen in accordance with a linear characteristic thereof. It is therefore necessary to hold the element temperature at a high temperature equal to or higher than about 600° C. in order to activate the sensor body 32. In a zone richer than the stoichiometric ratio, the concentration of unburned gases such as carbon monoxide (CO) changes almost linearly with the air-fuel ratio and the sensor body 32 generates a limit current according to the concentration of CO or the like.

Figure 3:
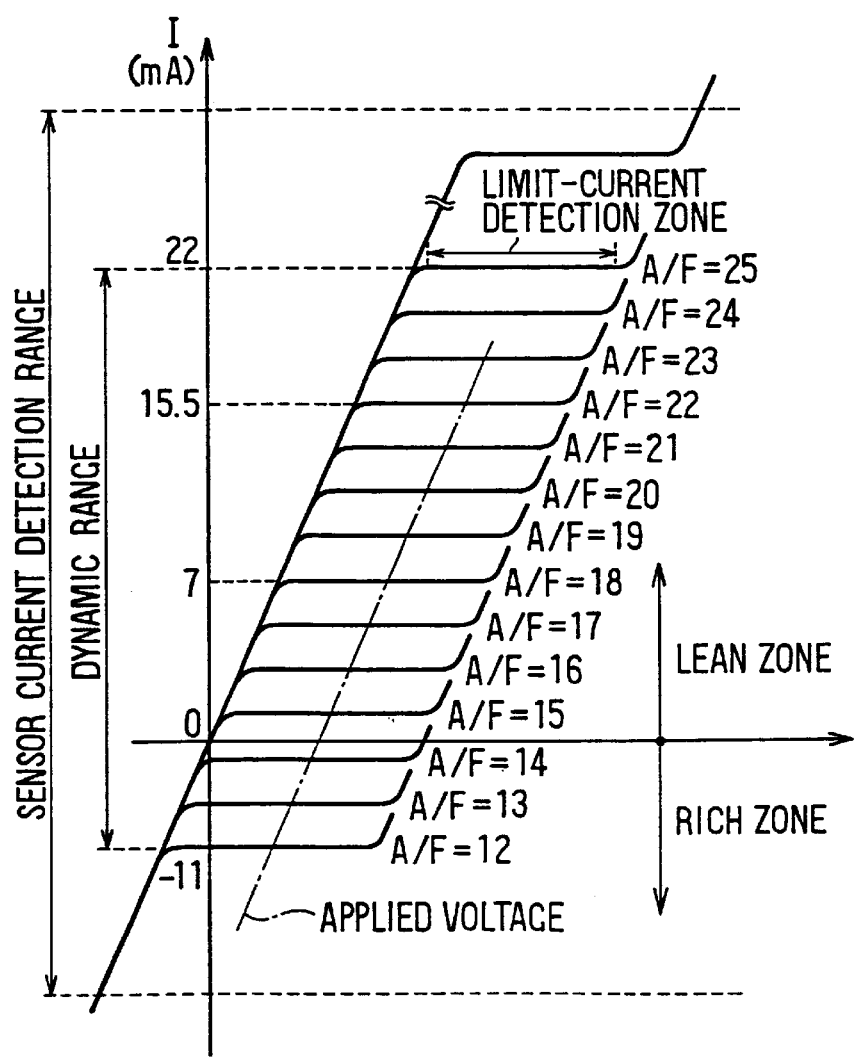
FIG. 3 is a graph showing a V-I characteristic of the A/F sensor.

It will be understood from FIG. 3 that current flowing in the solid electrolyte layer 34 of the sensor body 32, is proportional to the A/F detected by the A/F sensor 30 and changes linearly with respect to a voltage applied to the solid electrolyte layer 34. In this case, straight line segments parallel to the voltage axis V constitute a limit current limited detection zone which specifies the limit current of the sensor body 32. Increases and decreases of the limit current (sensor current) correspond to increases and decreases in the A/F (that is, the degree of lean and rich). That is, the more the A/F is shifted to the lean side, the more the limit current increases. The more the A/F is shifted to the rich side, the more the limit current decreases.

In the V-I characteristic, a voltage zone below the straight line segments (limit current detection zone) parallel to the voltage axis V is a resistance dominated zone. The gradient of the linear straight line segments in the resistance dominated zone is specified by the internal resistance (element resistance) of the solid electrolyte layer 34 in the sensor body 32. Since the element resistance changes with change in temperature, when the temperature of the sensor body 32 decreases, the gradient is reduced by the increase in the element resistance.

In the V-I characteristic of FIG. 3, a "sensor current detection range" is set between an extreme rich zone and an extreme lean zone and a "dynamic range" as an air-fuel ratio detection range is set within the sensor current detection range. According to the air-fuel ratio control system of this embodiment, since a lean-burn control is performed, the dynamic range is set in a range of A/F=12 to 25.

Referring back to FIG. 1, the bias control circuit 10 is a circuit for controlling a voltage applied to the A/F sensor 30 and has the following configuration. That is, the bias control circuit 10 has a reference voltage circuit 11. The reference voltage circuit 11 generates a predetermined reference voltage Va (2.5V in the embodiment) by dividing a constant voltage Vcc by voltage dividing resistors 12 and 13.

A voltage dividing point of the reference voltage circuit 11 at which the reference voltage Va exists is connected to a non-inversion input terminal of an amplifier 14a in an amplification circuit 14. One terminal 25 of the A/F sensor 30 is connected to the output terminal of the amplifier 14a via a sensor current detection circuit 15. The terminal 25 is a terminal connected to the atmosphere side electrode layer 37 in the A/F sensor 30. The same voltage Va (2.5V) as the reference voltage Va of the reference voltage circuit 11 is always applied to the terminal 25. The terminal 25 is connected to an inversion input terminal of the amplifier 14a and the voltage Va of the terminal 25 is received by the A/D converter 22.

The sensor current detection circuit 15 detects a sensor current Ip according to the air-fuel ratio at each time and has two current detection resistors 15a and 15b which are serially connected between the output terminal of the amplifier 14a and the terminal 25 of the A/F sensor 30. A voltage Vc at a connecting point (C point in the diagram) of the current detection resistors 15a and 15b is received by the A/D converter 22.

A CPU 21 for bias control receives voltages from both ends of the current detection resistor 15a through the A/D converter 22 and detects the sensor current (limit current) Ip at that time from the A/D-converted data of the both-end voltages (Va and Vc). The CPU 21 computes an instruction value of a voltage for applying to the A/F sensor 30 in accordance with the sensor current Ip at that time. Specifically, an application voltage linear line Lx shown in FIG. 3 is used and an application voltage according to the sensor current Ip at that time is determined. The voltage instruction value calculated by the CPU 21 is converted to an instruction voltage Vb by a D/A converter 23 and the instruction voltage Vb after the D/A conversion is applied to an amplification circuit 16.

The D/A converter 23 is connected to the non-inversion input terminal of an amplifier 16a in the amplification circuit 16. An inversion input terminal of the amplifier 16 and the other terminal 26 of the A/F sensor 30 are connected to the output terminal of the amplifier 16a. In this case, the terminal 26 is a terminal connected to the exhaust-side electrode layer 36 of the A/F sensor 30 and the same voltage Vb as the instruction voltage Vb as an output of the D/A converter 23 is applied to the terminal 26.

At the time of the air-fuel ratio detection, therefore, in the bias control circuit 10 having the above construction, the reference voltage Va is always supplied to the terminal 25 which is one of the terminals of the A/F sensor 30 and the instruction voltage Vb is applied to the other terminal 26. When the instruction voltage Vb supplied to the other terminal 26 of the A/F sensor 30 via the D/A converter 23 is lower than the reference voltage Va (if Vb<Va), a positive bias is applied to the A/F sensor 30. If the instruction voltage Vb supplied to the other terminal 26 of the A/F sensor 30 is higher than the reference voltage Va (if Vb>Va), a negative bias is applied to the A/F sensor 30. In either case, the sensor current Ip which flows with the application of voltage is detected as a difference (Vc−Va) between the electric potentials of the ends of the current detection resistor 15a and is supplied to the CPU 21 by way of the A/D converter 22.

In addition, the bias control circuit 10 has a voltage follower 17 for receiving the sensor current Ip flowing the current detection circuit 15 as a voltage signal and outputting the received voltage signal to an engine control ECU 40 on the outside. The point C or the point D in the diagram is connected to the non-inversion input terminal of the voltage follower 17 in accordance with the switched position of a switch circuit 18. The point C is a connecting point of the current detection resistors 15a and 15b and the point D is a connecting point of the output terminal of the amplifier 14a and the current detection resistor 15b.

In this case, when the switch circuit 18 is turned to the voltage Vc side as shown in the diagram, the voltage Vc at the point C is used as a voltage Vf at the non-inversion input terminal of the voltage follower 17. That is, the sensor current Ip flowing through the current detection resistors 15a and 15b is detected only by the resistance of the current detection resistor 15a and the voltage Vc corresponding to Ip is supplied to the voltage follower 17 via the switch circuit 18.

When the switch circuit 18 is changed from the position shown in the diagram to the voltage Vd side, the voltage Vd at the point D is used as the voltage Vf at the non-inversion input terminal of the voltage follower 17. That is, the sensor current Ip is detected by the resistance of the current detection resistors 15a and 15b and the voltage Vd corresponding to Ip is supplied to the voltage follower 17 via the switch circuit 18. The switching operation of the switch circuit 18 is performed by the CPU 21.

The voltage output of the voltage follower 17 is inputted to a CPU 42 via an A/D converter 41 in the engine control ECU 40. The CPU 42 detects an actual air-fuel ratio on the basis of the difference between the A/F value (voltage value) inputted via the A/D converter 41 and the reference voltage Va of the bias control circuit 10. In the A/D converter 41 of this embodiment, the power source voltage is a constant voltage Vcc of "5V" (not shown in the diagram) and the input voltage range which can be read by the A/D converter 41 is set to "0 to 5V". In this case, if the 8-bit A/D converter 41 is used, the input voltage range of "0 to 5V" is divided into 256 to read the A/F values.

With respect to the air-fuel ratio F/B control by the engine control ECU 40, since it is not the gist of the case and the control is known, its detailed description is omitted here. The engine control ECU 40 receives the detection result (voltage signal) of the air-fuel ratio by the A/F sensor 30 and F/B controls the air-fuel ratio in accordance with a control algorithm such as the advanced control or a PID control on the basis of the detection result. The engine control ECU 40 controls the amount of fuel injected from an injector (not shown) to each of cylinders of the engine so that the air-fuel ratio at each time coincides with the target air-fuel ratio. In this instance, if the engine is in a low load state, lean-burn control is performed and if the engine is in an intermediate or high load state, an ordinary stoichiometric control is executed.

The switching operation of the switch circuit 18 will be described by showing actual specific values. Methods of detecting the air-fuel ratio with respect to the following two zones will be described here;

A zone (A/F=12.8 to 18) near the stoichiometric ratio in the dynamic range

Other air-fuel ratio zones (A/F=12 to 12.8, 18 to 25) In the apparatus according to this embodiment, the zone near the stoichiometric ratio where A/F=12.8 to 18 corresponds to the air-fuel ratio detection range which is necessary at the time of the stoichiometric control and the air-fuel ratio zone where A/F=18 to 25 corresponds to the air-fuel ratio detection range which is necessary at the time of lean-burn control.

The reference voltage Va is set to "2.5V", the sensor current Ip when A/F=18 is set to "7 mA", and the sensor current Ip when A/F=25 is set to "22 mA" (V-I characteristic of FIG. 3). A resistance value R1 of the current detection resistor 15a is set to "113 Ω" and a resistance value R2 of the current detection resistor 15b is set to "224 Ω".

Figure 1:
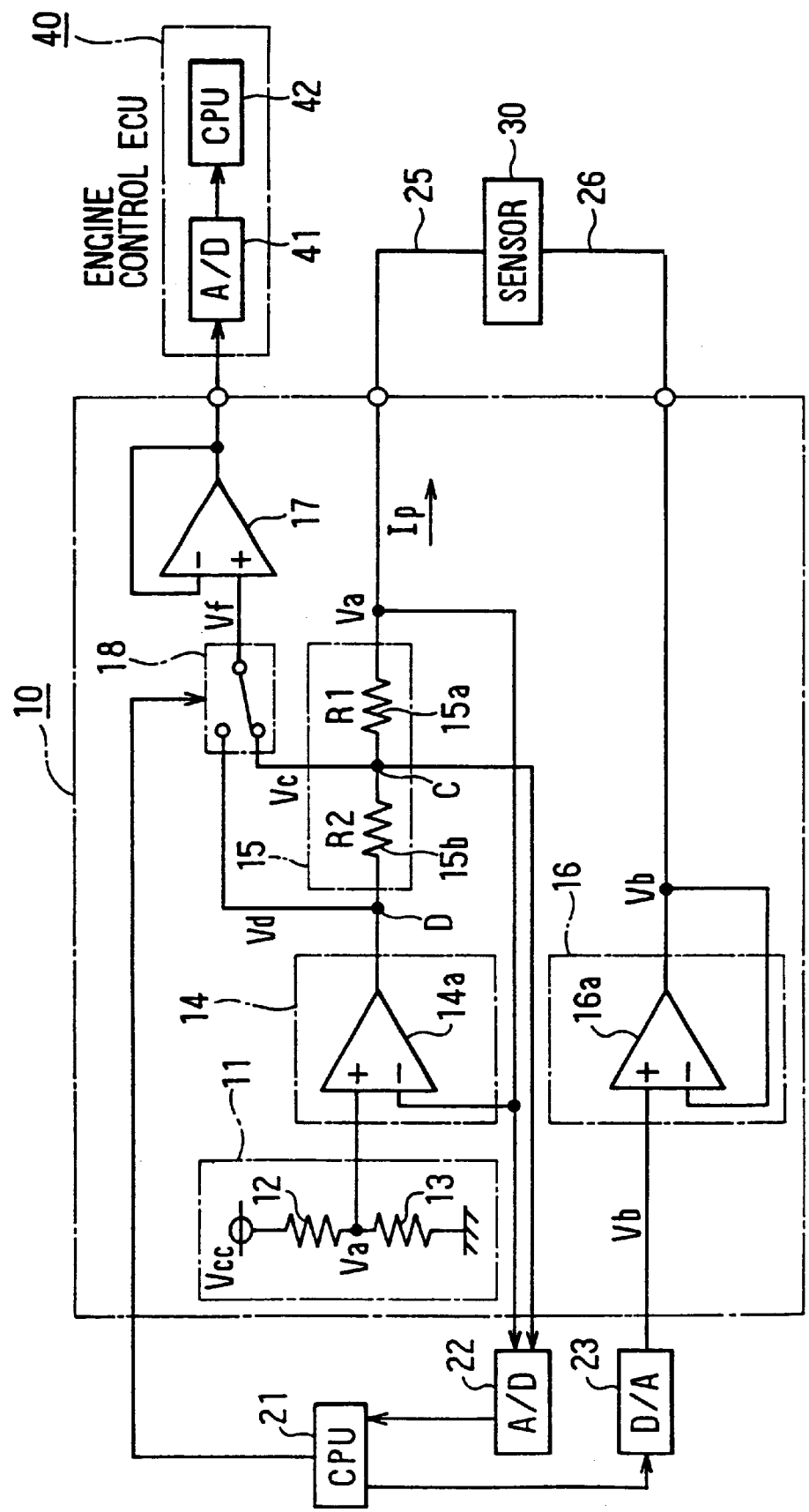
FIG. 1 is a circuit diagram showing an air-fuel ratio detecting apparatus used as a gas concentration detecting apparatus according to a first embodiment of the present invention.

First, in the zone (A/F=12.8 to 18) near the stoichiometric ratio, the air-fuel ratio at which the voltages Vc and Vd at the points C and D in FIG. 1 are maximum is A/F=18. The voltages Vc and Vd when A/F=18 are Vc=3.291V, and Vd=4.999V.

In connection, the voltage Vc is obtained by adding the reference voltage Va to the product of the sensor current Ip and the resistance value R1 of the current detection resistor 15a (Vc=Ip·R1+Va). The voltage Vd is obtained by adding the reference voltage Va to the product of the sensor current Ip and the resistance values R1+R2 of the current detection resistors 15a and 15b (Vd=Ip·(R1+R2)+Va).

Since both of the values of the voltages Vc and Vd are within the voltage range (0 to 5V) which can be dealt by the A/D converter 41 in the engine control ECU 40, both of the values can be read by the A/D converter 41. In order to assure the detection accuracy of the air-fuel ratio as described above, it is preferable to set the voltage value per unit A/F as large as possible.

When the voltage values of the voltages Vc and Vd per unit A/F are calculated by using the stoichiometric ratio (A/F=14.7) as a reference, the voltage value per unit A/F of the voltage Vc is obtained as "0.239V" from the following arithmetic expression.

(3.291V−2.5V)/(18−14.7)

The voltage value per unit A/F of the voltage Vd is obtained as "0.757V" from the following arithmetic expression.

(4.999V−2.5V)/(18−14.7)

In this case, the fact that the latter has the larger voltage value per unit A/F denotes the voltage Vd has higher detection accuracy than the voltage Vc. There is a similar tendency for any air-fuel ratio if it is within the zone (A/F=12.8 to 18) near the stoichiometric ratio. That is, in the zone near the stoichiometric ratio, by using the Vd value as the input voltage Vf of the voltage follower 17, the detection accuracy of the air-fuel ratio can be assured.

Figure 4:
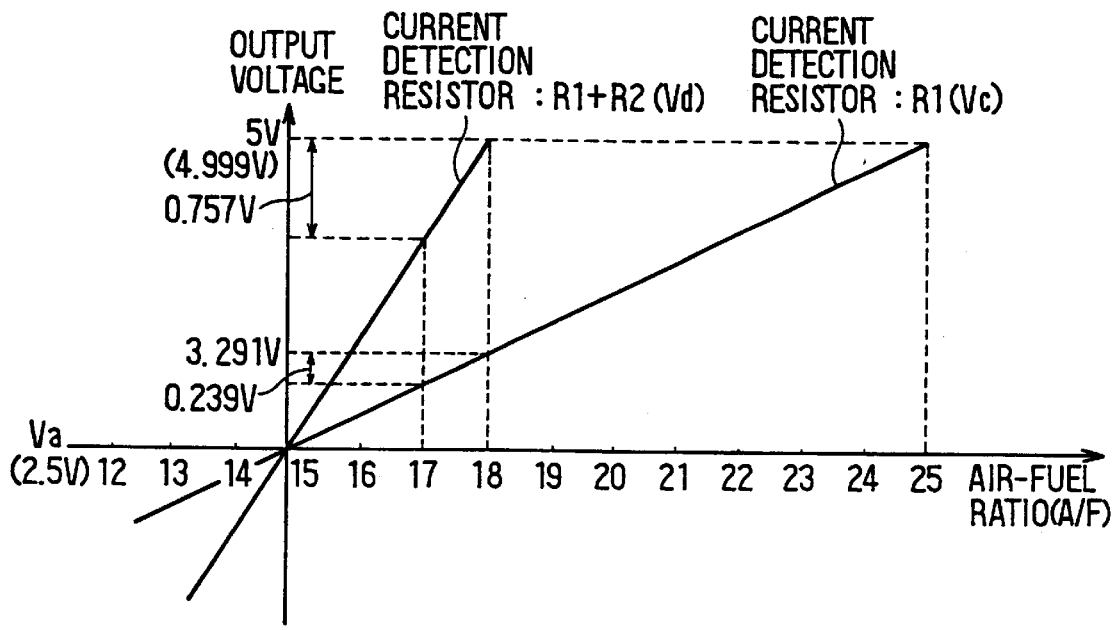
FIG. 4 is a graph showing an output voltage characteristics of the A/F sensor for each air-fuel ratio.

This output voltage characteristic will be described with reference to FIG. 4. If the voltage value per unit A/F when A/F=18 of a case where the value of the current detection resistor is "R1" (in case of outputting the voltage Vc) is compared with that of a case where the value of the current detection resistor is "R1+R2" (in case of outputting the voltage Vd), it will be understood that the latter one is larger and the detection accuracy of the air-fuel ratio is improved.

On the other hand, in the air-fuel ratio zones (A/F=12 to 12.8, 18 to 25) other than the zone near the stoichiometric ratio, the air-fuel ratio at which the voltages Vc and Vd at the points C and D in FIG. 1 are maximum is A/F=25. The voltages Vc and Vd when A/F=25 are as follows.

Vc=4.986V

Vd=10.354V (Vc=Ip·R1+Va, Vd=Ip·(R1+R2)+Va)

In this case, since the input voltage range of the A/D converter 41 is "0 to 5V", although the voltage Vc can be read, the voltage Vd cannot be read. In the air-fuel ratio zones (A/F=12 to 12.8, 18 to 25) other than the zone near the stoichiometric ratio, the Vc value is used as the input voltage Vf of the voltage follower 17. That is, as shown in the output voltage characteristic of FIG. 4, the value of the current detection resistor has to be set to "R1" (value of the current detection resistor 15a). Thus, the air-fuel ratio of a maximum is detected.

Figure 5:
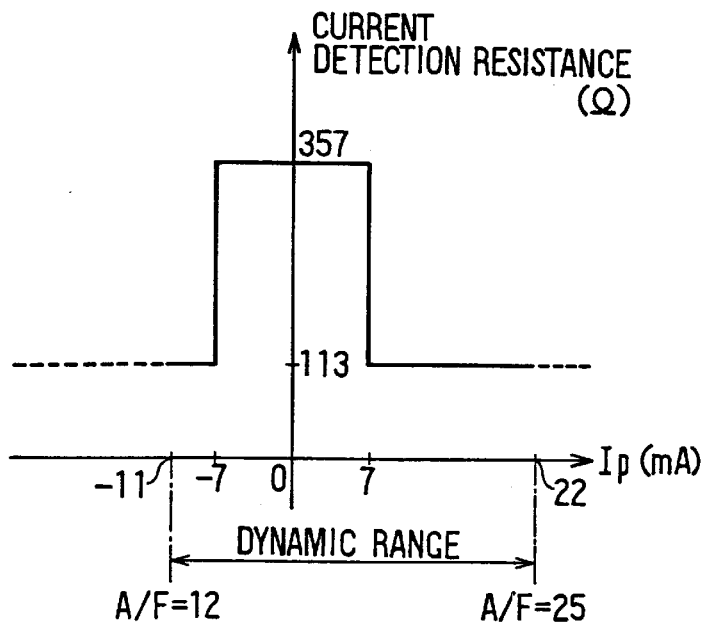
FIG. 5 is a graph showing a relation between a sensor current and a current detection resistor in the first embodiment.

FIG. 5 is a graph showing a preferable relation between the sensor current Ip (mA) and the resistance (Ω) of the current detection resistor according to the Ip value. In the diagram, Ip=−11 mA when A/F=12, Ip=−7 mA when A/F= 12.8, Ip=7 mA when A/F=18, and Ip=22 mA when A/F=25. According to the diagram, it is understood that it is sufficient that the current detection resistance is set to "357 Ω" corresponding to the value of "R1+R2" when −7 mA≦Ip≦7 mA (when A/F=12.8 to 18), and the current detection resistance is set to "113 Ω" corresponding to the value of "R1" in the case where −11 mA≦Ip<−7 mA and 7 mA<Ip≦22 mA (in case of A/F=12 to 12.8, 18 to 25).

Figure 6:
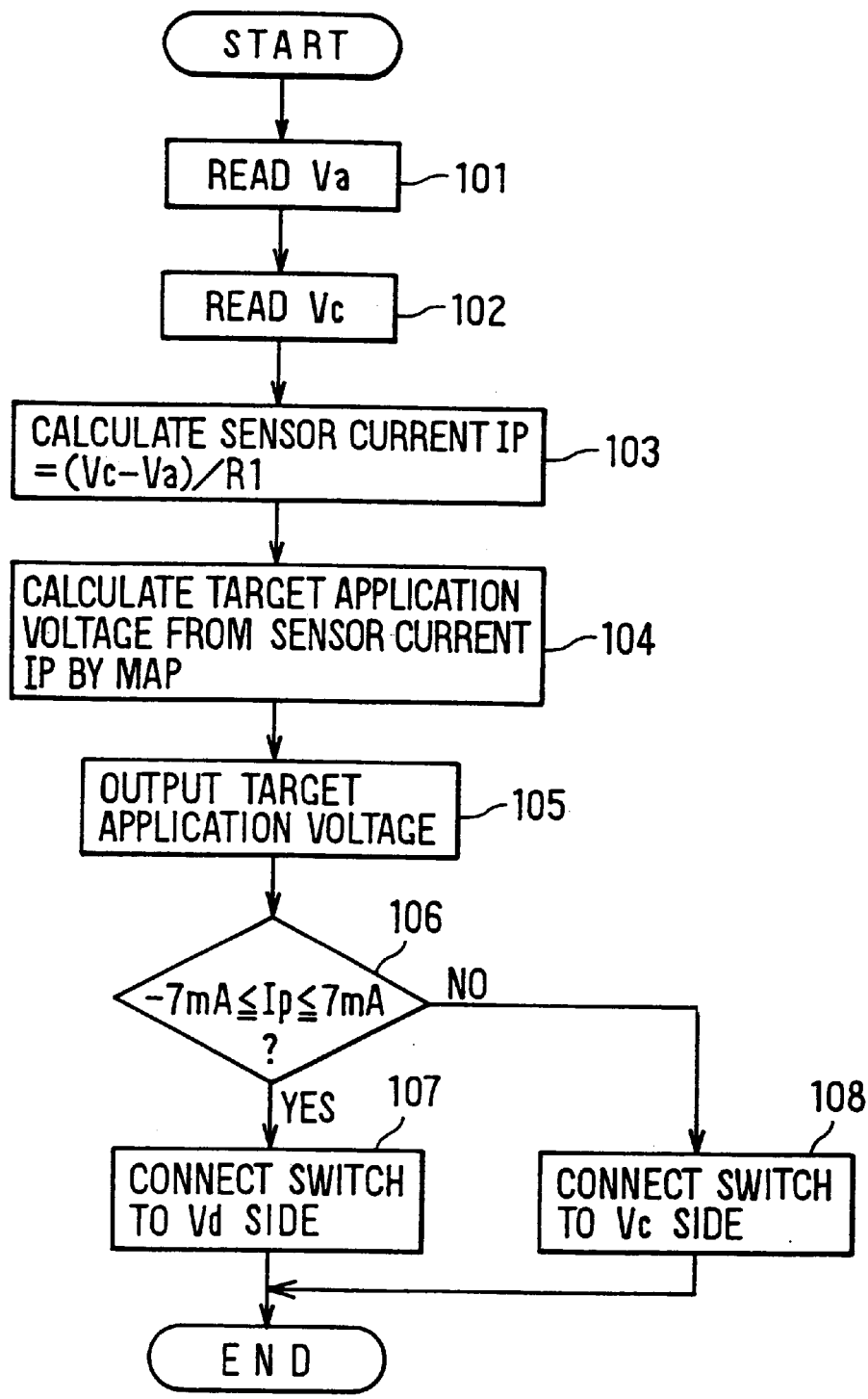
FIG. 6 is a flowchart showing an air-fuel ratio detecting routine in the first embodiment.

The operation of the air-fuel ratio detecting apparatus constructed as mentioned above will be described. FIG. 6 is a flowchart showing an air-fuel ratio detecting routine executed by the CPU 21. The CPU 21 repeatedly executes the routine in a predetermined cycle (for example, at intervals of 4 ms).

The CPU 21 detects the sensor current Ip flowing according to the air-fuel ratio at each time in steps 101 to 103. In detail, the CPU 21 reads one terminal voltage Va of the current detection resistor 15a via the A/D converter 22 in step 101. In the following step 102, the other terminal voltage Vc of the current detection resistor 15a is read via the A/D converter 22. After that, in step 103, the CPU 21 calculates the present sensor current Ip on the basis of the voltages Va and Vc read through the A/D converter 22 by using the operational equation Ip=(Vc−Va)/R1

(where, R1 is a resistance value of the current detection resistor 15a).

Then, the CPU 21 obtains a target application voltage corresponding to the calculated sensor current Ip by using the application voltage characteristic line Lx shown in FIG. 3 in step 104 (map calculation). Further, in step 105, the CPU 21 applies the obtained target application voltage as a voltage instruction value (instruction voltage Vb) via the D/A converter 23 to the A/F sensor 30.

The CPU 21 discriminates whether the sensor current Ip at that time lies within a range of "−7 mA to 7 mA" or not in step 106. Ip=−7 mA, 7 mA are thresholds used to discriminate whether the air-fuel ratio at that time is in the zone near the stoichiometric ratio (A/F=12.8 to 18) or not. If the step 106 is affirmatively discriminated, it denotes that the air-fuel ratio at that time lies within the zone near the stoichiometric ratio.

When the step 106 is affirmatively discriminated (in case of −7 mA≦Ip≦7 mA), the CPU 21 connects the switch circuit 18 to the voltage Vd side in step 107. Consequently, the voltage Vd serves as the input voltage Vf of the voltage follower 17 and the Vd value is outputted as an A/F output to the A/D converter 41 in the engine control ECU 40. In this instance, the A/F output detected by the sensor current detection circuit 15 is detected by the sum "R1+R2" of both of the resistance values of the current detection resistors 15a and 15b.

When the step 106 is negatively discriminated, the CPU 21 allows the switch circuit 18 to be connected to the voltage Vc side in step 108. Consequently, the voltage Vc serves as the input voltage Vf of the voltage follower 17 and the Vc value is ID outputted as an A/F output to the A/D converter 41 in the engine control ECU 40. In this instance, the A/F output detected by the sensor current detection circuit 15 is detected by the resistance value "R1" of the resistor 15a which is one of the current detection resistors.

On the other hand, in the air-fuel ratio detecting apparatus according to this embodiment, the output value is adjusted by the following procedures in the manufacturing process of the apparatus to eliminate individual variations from apparatus to apparatus. The air-fuel ratio output signal (output signal of the voltage follower 17) of the bias control circuit 10 causes detection errors for the following reasons.

(1) variations of the resistors 12 and 13 of the reference voltage circuit 11, (2) offset error of the operational amplifiers 14a and 17, (3) variation of the sensor current detection circuit 15, and the like.

The procedure for adjusting the output voltage is explained with reference to FIGS. 7 and 8. Here, the reference voltage Va of the A/F sensor 30 determined by the voltage dividing resistors 12 and 13 in the reference voltage circuit 11 is "2.5V", the resistance value of the sensor current detection circuit 15 is "357 Ω", the sensor current at A/F=18 is "7 mA", the sensor current at A/F=17 is "4.880 mA". In this instance, the output voltage at A/F=18 is:

357 Ω·7 mA+2.5V=4.999V

Further, the output voltage at A/F=17 is:

357 Ω·4.880 mA+2.5V=4.242V

Therefore, the width of the voltge for the unit A/F (1 A/F) is 0.757V (=4.999–4.242).

To be more specific with regard to the above variations (1)–(3), because the voltage dividing resistors 12 and 13 have variations of about ±1%, the reference voltage Va varies within a range of 1% (that is, ±25 mV) of 2. (above (1)).

Further, because the operational amplifiers 14a and 17 have the offset voltage Voff of about ±20 mV, an error occurs between the positive (+) side and negative (−) side terminls in each of the operational amplifiers 14a and 17 (abobe variations (2)). The sum of the errors (offset voltage Voff) of the two operational amplifiers 14a and 17 amounts to about ±40 mV.

Still further, in the sensor current detection circuit 15, the current detection resistors 15a and 15b have variations of about ±1%. As a result, voltage error corresponding to the variations of the sensor current and the current detection resistors 15a and 15b occurs at other than the stoichiometric ratio where the sensor current becomes OmA. For instance, the error at A/F=17 is:

4.880 mA·357 Ω·0.01=17.4 mV (above (3)).

The maximum sum of the errors of the above (1) to (3) at A/F=17 is:

25 mV+40 mV+17.4 mV=82.4 mV

Figure 7:
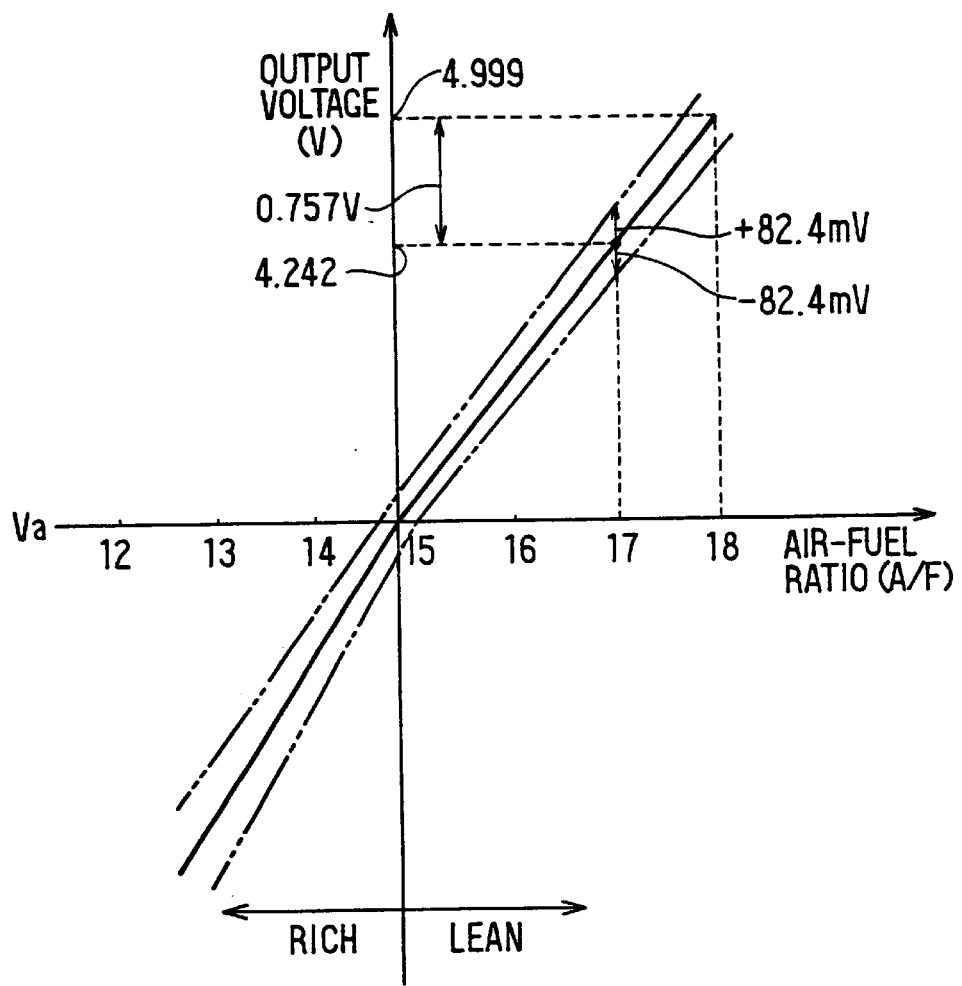
FIG. 7 is a graph showing an error in the output voltage of the air-fuel ratio detecting apparatus.

That is, as shown in FIG. 7, the relation between the air-fuel ratio and the output voltage includes variations shown by the two-dot chain line against an ideal characteristics shown by the solid line due to the above reasons (1) to (3). At A/F=17, the error becomes ±82.4 mV at maximum against the ideal output voltage. This output voltage error corresponds to A/F error of:

82.4 mv/0.757V=0.11

According to the present embodiment, therefore, the voltage dividing resistors 12 and 13 of the reference voltage circuit 11 in the bias control circuit 10 are trimmed appropriately to obviate individual vatiation of the device caused by the above errors. Though the circuit shown in FIG. 8 has the same construction as the bias control circuit 10 shown in FIG. 1, its construction such as the sensor current detection circuit 15 is shown in a simplified form partly for brevity.

Specifically, a constant current source 101 is connected to the terminal 100 of the bias control circuit 10 to provide a current of a constant value by the constant current source. For instance, with a current of "4.880 mA" which corresponds to A/F=17 being provided, the output voltage of the bias control circuit 10 (potential at Z-point in FIG. 8) is measured. at this time, the voltage dividing resistor 12 or 13 is trimmed in accordance with the deviation of the output voltage at the Z-point from the ideal vlaue "4.242V" of the output voltage at A/F=17.

If the output voltage measured at the Z-point is higher than the ideal value "4.242V", the voltage dividing resistor 12 is trimmed. By trimmimg the voltage dividing resistor 12 to a larger resistance, the reference voltage Va produced from the reference voltage circuit 11 is decreased. As the output voltage at the Z-point decreases in proportion to the reference voltage Va, the output voltage of the Z-point is made closer to the ideal value by trimming the voltage dividing resistor 12. This procedure enables provision of the ouput voltage which has the least variation from the ideal value.

If the output voltage measured at the Z-point is lower than the ideal value "4.242V" at A/F=17, the voltage dividing resistor 13 is trimmed. By trimmimg the voltage dividing resistor 13 to a larger resistance, the reference voltage Va produced from the reference voltage circuit 11 is increased. Thus, the voltage of the Z-point is made closer to the ideal value to provide the ouput voltage which has the least variation from the ideal value. The voltage dividing resistors 12 and 13 may be trimmed by thick film resistor trimming method, thin film resistor trimming method which can be performed on a chip or the like trimming method.

According to the embodiment described in detail, the following effects can be obtained.

(a) According to this embodiment, in the air-fuel ratio detecting apparatus for converting the sensor current Ip into a voltage signal and outputting the voltage signal to the A/D converter 41 via the voltage follower 17, the resistance value of the sensor current detection circuit 15 for sending the voltage signal to the voltage follower 17 is variably set in accordance with the sensor current Ip. According to the construction, the air-fuel ratio can be always detected in the voltage range which can be read by the A/D converter 41, that is, the voltage range of "0 to 5V". Further, a high detection accuracy can be assured within a limitation that the air-fuel ratio should be detected in the above voltage range. Consequently, the detection accuracy of the air-fuel ratio can be improved even when a wide air-fuel ratio detection range is required. As a result, also in the air-fuel ratio control system in which both of stoichiometric control and lean-burn control are performed, the detection accuracy of the air-fuel ratio near the stoichiometric ratio can be improved while assuring the detection accuracy of the air-fuel ratio at the time of the lean-burn control.

(b) According to embodiment, the current detection resistors 15a and 15b are constructed by a plurality of resistors whose resistance values are known and the resistor connected to the input terminal of the voltage follower 17 is properly changed in accordance with the sensor current Ip. In this case, by switching the resistance value by the switch circuit 18, the switching operation can be realized with a simple construction.

(c) Further, the resistance value of the current detection resistor is changed for each zone by dividing into a plurality of air-fuel ratio zones an (air-fuel ratio zone having a center at the target air-fuel ratio) with respect to the target air-fuel ratio (A/F=14.7, 22) at time of the stoichiometric control or lean-burn control as a reference. Thus, the detection accuracy as required can be assured at the air-fuel ratio point where air-fuel ratio detection accuracy is required.

(d) In an air-fuel ratio control system using air-fuel ratio detecting apparatus with the above construction, since the detection accuracy of the A/F value as a control parameter is enhanced, air-fuel ratio F/B control with high accuracy can be realized and excellent effects such that emission and fuel consumption is reduced can be obtained.

(e) The switch circuit 18 for switching the resistnce value of the sensor current detection circuit 15 is provided not in the sensor current flow path but at the input side of the voltage follower 17. In this instance, the disadvantage that the air-fuel ratio detection acuracy degrades due to variations in the current signal caused by a resistance component of the switch circuit 18 can be obviated.

(f) Further, at the time of manufacturing the air-fuel ratio detecting apparatus, the output voltage of the voltage follower 17 is monitored and the voltage dividing resistors for the reference voltage are trimmed appropriately to adjust the output voltage. As a result, variations in output arising from the individual variation of the air-fuel ratio detecting apparatus (bias control circuit 10) can be reduced and accuracy in the air-fuel ratio detection can be enhanced to a higher level.

The second to sixth embodiments of the invention will now be described. In each of the following embodiments, portions equivalent to those in the above-mentioned first embodiment are designated by the same numerals and their descriptions are simplified. The points different from the first embodiment will be mainly described hereinbelow.

(Second embodiment)

Figure 9:
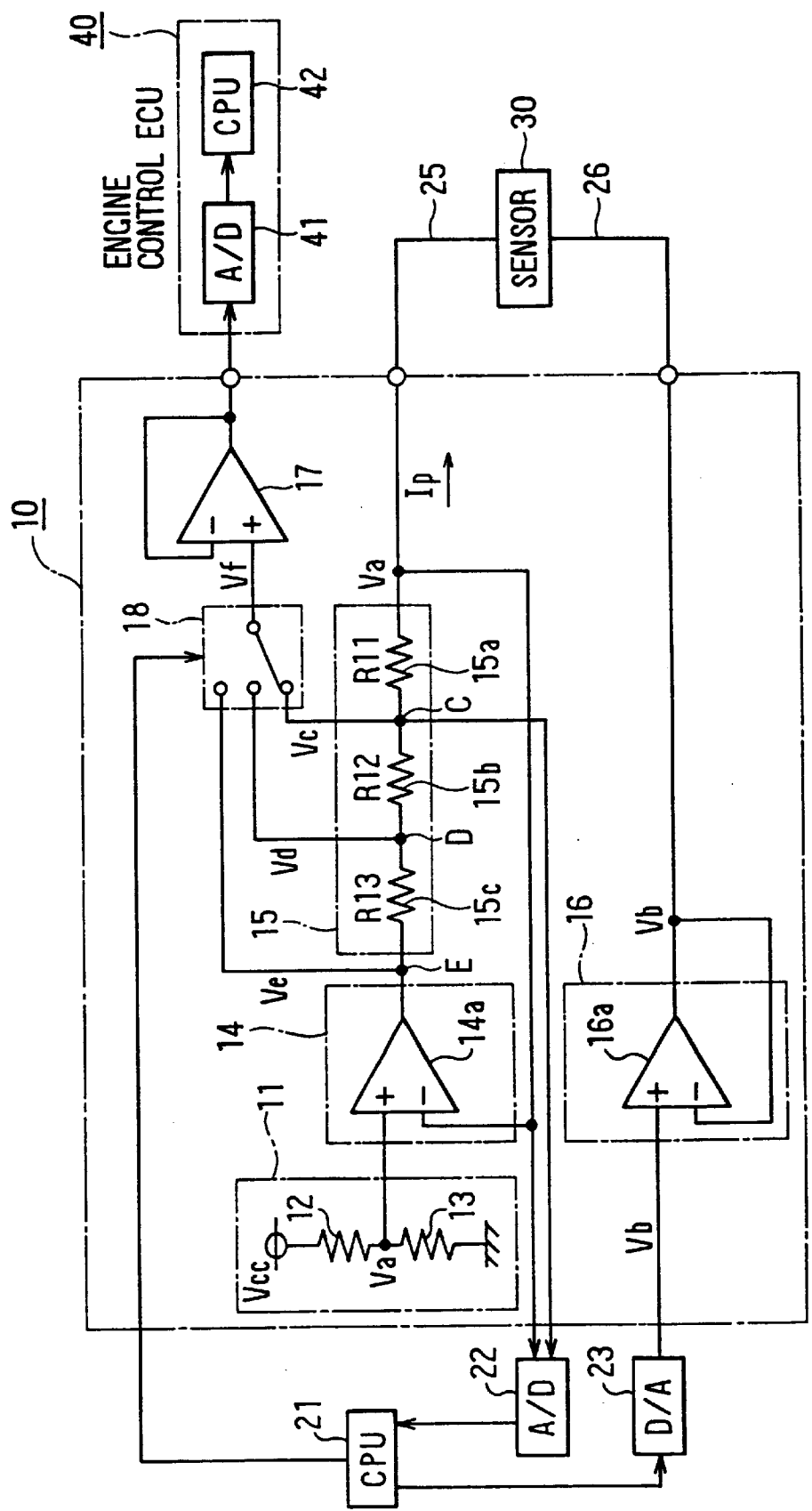
FIG. 9 is a circuit diagram showing an air-fuel ratio detecting apparatus according to a second embodiment of the present invention.
Figure 10:
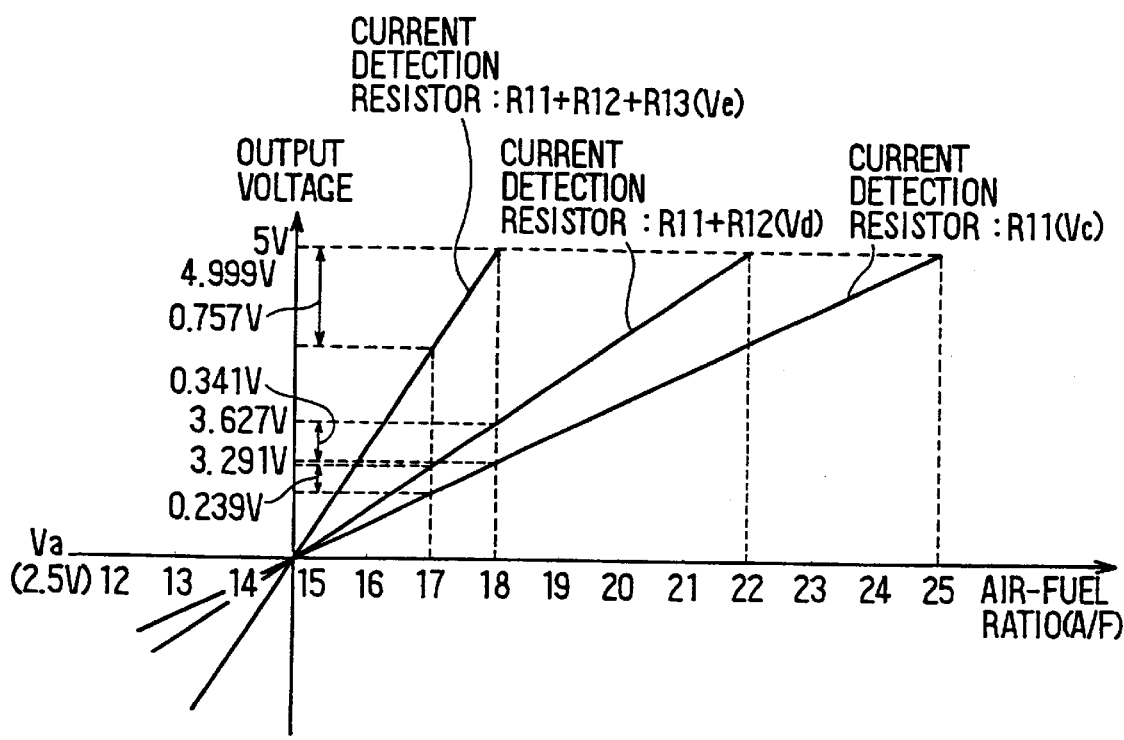
FIG. 10 is a graph showing an output voltage characteristic for each air-fuel ratio in the second embodiment.

The second embodiment of the invention will be described with reference to FIGS. 9 to 10. FIG. 9 is a circuit diagram showing the outline of an air-fuel ratio detecting apparatus in the embodiment. Since the construction of the apparatus is basically similar to that of FIG. 1 of the first embodiment, only different points will be described hereinbelow.

A sensor current detection circuit 15 has three current detection resistors 15a, 15b, and 15c which are serially connected between the output terminal of the amplifier 14a and the terminal 25 of the A/F sensor 30. The point C, D, or E in the diagram is connected to the non-inversion input terminal of the voltage follower 17 which receives the sensor current Ip as a voltage signal in accordance with the switching position of a switch circuit 52. The point C is a connecting point of the current detection resistors 15a and 15b. The point D is a connecting point of the current detection resistors 15b and 15c. The point E is a connecting point of the output terminal of the amplifier 14a and the current detection resistor 15c.

In this case, when the switch circuit 52 is turned to the voltage Vc side as shown in the diagram, the voltage Vf of the input terminal of the voltage follower 17 becomes the voltage Vc at the point C. That is, the sensor current Ip flowing in the sensor current detection circuit 15 is detected only by the resistance of the current detection resistor 15a. The voltage Vc corresponding to Ip is supplied to the voltage follower 17 via the switch circuit 52.

When the switch circuit 52 is changed from the position shown in the diagram to the voltage Vd side, the voltage Vf of the input terminal of the voltage follower 17 becomes the voltage Vd at the point D. That is, the sensor current Ip is detected by the resistance of the current detection resistors 15a and 15b and the voltage Vd corresponding to Ip is supplied to the voltage follower 17 via the switch circuit 52.

Further, when the switch circuit 52 is changed from the position shown in the diagram to the voltage Ve side, the voltage Vf of the input terminal of the voltage follower 17 becomes the voltage Ve at the point E. That is, the sensor current Ip is detected by the resistance of the current detection resistors 15a, 15b, and 15c. The voltage Ve corresponding to this Ip is supplied to the voltage follower 17 via the switch circuit 52.

The switching operation of the switch circuit 52 is controlled by the CPU 21 in a manner similar to the first embodiment. The switching operation of the switch circuit 52 will be described by showing actual specific values. Methods of detecting the air-fuel ratio will be described here with respect to each of the following three zones.

first air-fuel ratio zone (A/F=12.8 to 18) as a zone near the stoichiometric ratio in the dynamic range second air-fuel ratio zone (A/F=12 to 12.8, 18 to 22) as zones outside of the first air-fuel ratio zone third air-fuel ratio zone (A/F=22 to 25) as a zone outside of the second air-fuel ratio zone.

In the embodiment, the reference voltage Va is "2.5V", the sensor current Ip when A/F=18 is "7 mA", the sensor current Ip when A/F=22 is "15.5 mA", and the sensor current Ip when A/F=25 is "22 mA" (V-I characteristic of FIG. 3). A resistance value R11 of the current detection resistor 15a is set to "113 Ω", a resistance value R12 of the current detection resistor 15b is set to "148 Ω", and a resistance value R13 of the current detection resistor 15c is set to "196 Ω".

In the first air-fuel ratio zone (A/F=12.8 to 18), the air-fuel ratio at which the voltages Vc, Vd, and Ve at the points C, D, and E in FIG. 9 are maximum is A/F=18. The voltages Vc, Vd, and Ve when A/F=18 are as follows.

$$Vc=3.291V$$

$$Vd=3.627V$$

$$Ve=4.999V$$

The voltage Vc is obtained by adding the reference voltage Va to the product of the sensor current Ip and the resistance value R11 of the current detection resistor 15a (Vc=Ip·R11+Va). The voltage Vd is obtained by adding the reference voltage Va to the product of the sensor current Ip and the resistance values (R11+R12) of the current detection resistors 15a and 15b (Vd=Ip·(R11+R12)+Va). The voltage Ve is obtained by adding the reference voltage Va to the product of the sensor current Ip and the resistance values (R11+R12+R13) of the current detection resistors 15a, 15b, and 15c (Ve=Ip·(R11+R12+R13)+Va).

Since all of the values of the voltages Vc, Vd, and Ve are within a voltage range (0 to 5V) which can be dealt by the A/D converter 41 in the engine control ECU 40, each value can be read by the A/D converter 41. As described before, however, in order to assure detection accuracy of the air-fuel ratio, it is desirable to increase the voltage value per unit A/F as much as possible.

When the voltage value per unit A/F of each of the voltages Vc, Vd, and Ve is calculated by using the stoichiometric ratio (A/F=14.7) as a reference, the voltage value per unit A/F of the voltage Vc is obtained as "10.239V" from the following arithmetic expression.

$$(3.291V-2.5V)/(18-14.7)$$

The voltage value per unit A/F of the voltage Vd is obtained as "0.341V" from the following arithmetic expression.

$$(3.627V-2.5V)/(18-14.7)$$

The voltage value per unit A/F of the voltage Ve is obtained as "0.757V" from the following arithmetic expression.

$$(4.999V-2.5V)/(18-14.7)$$

In this case, since the voltage value per unit A/F of the voltage Ve is the largest, it can be the that the voltage Ve has highest detection accuracy. There is a similar tendency for any A/F values if it is within the zone near the stoichiometric ratio (A/F=12.8 to 18). That is, in the zone near the stoichiometric ratio, the Ve value is used as the input voltage Vf of the voltage follower 17, thereby enabling the detection accuracy of the air-fuel ratio to be assured.

The output voltage characteristic will be described with reference to FIG. 10. If the voltage value per unit A/F when A/F=18 is compared with respect to each of:
(a) a case where the value of the current detection resistance is set to "R11" (in case of outputting the voltage vc),
(b) a case where the value of the current detection resistance is set to "R11+R12" (in case of outputting the voltage Vd), and
(c) a case where the value of the current detection resistance is set to "R11+R12+R13" (in case of outputting the voltage Vd),
it will be understood that the value of (c) is the largest and the detection accuracy of the air-fuel ratio is improved.

On the other hand, in the second air-fuel ratio zone (A/F=12 to 12.8, 18 to 22), the air-fuel ratio at which the voltages Vc, Vd, and Ve at the points C, D, and E in FIG. 9 are maximum is A/F=22. The voltages Vc, Vd, and Ve when A/F=22 are as follows.

$$Vc=4.251V$$

$$Vd=4.996V$$

$$Ve=8.034V$$

In this case, since the input voltage range of the A/D converter 41 in the engine control ECU 40 is "0 to 5V", the voltages Vc and Vd excluding Ve are readable values. When the voltages Vc and Vd are compared, the air-fuel ratio can be detected with higher accuracy by using the voltage Vd (reason is similar to that when A/F=18). In the second air-fuel ratio zone (A/F=12 to 12.8, 18 to 22), therefore, the Vd value is used as the input voltage Vf of the voltage follower 17. That is, as shown by the output voltage characteristic of FIG. 10, it is sufficient that the value of the current detection resistor is "R11+R12" (an addition value of the current detection resistors 15a and 15b).

Further, in the third air-fuel ratio zone (A/F=22 to 25), the air-fuel ratio at which the voltages Vc, Vd and Ve at the points C, D and E in FIG. 9 are maximum is A/F=25. The voltages Vc, Vd, and Ve when A/F=25 are as follows.

$$Vc=4.986V$$

$$Vd=6.042V$$

$$Ve=10.354V$$

In this case, since the input voltage range of the A/D converter 41 is "0 to 5V", although the voltage Vc can be read, the voltages Vd and Ve cannot be read. In the third air-fuel ratio zone (A/F=22 to 25), therefore, the Vc value is used as the input voltage Vf of the voltage follower 17. That is, as shown by the output voltage characteristic of FIG. 10, it is sufficient that the value of the current detection resistor is "R1" (value of the current detection resistor 15a).

Figure 11:
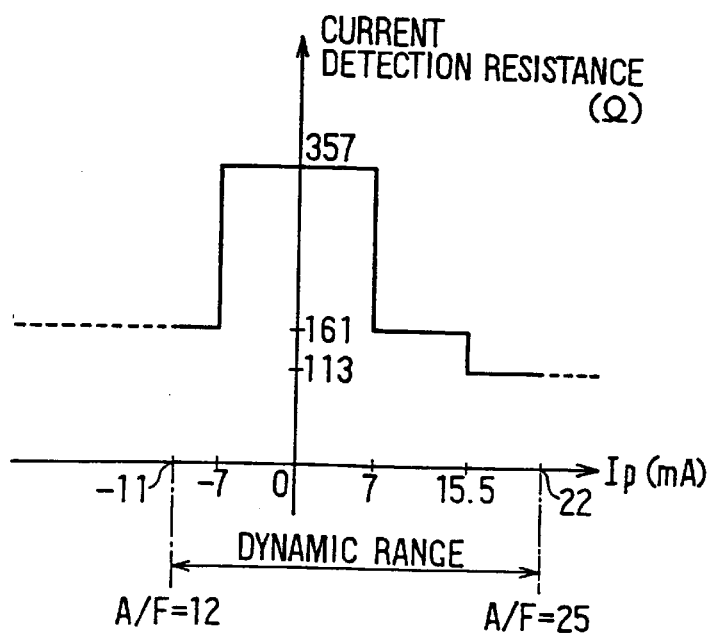
FIG. 11 is a graph showing the relation between the sensor current and the current detection resistor in the second embodiment.

FIG. 11 is a graph showing a preferable relation between the sensor current Ip (mA) and the resistance (Ω) of the current detection resistor according to the Ip value. In the diagram, Ip=−11 mA when A/F=12, Ip=−7 mA when A/F=12.8, Ip=7 mA when A/F=18, Ip=15.5 mA when A/F=22, and Ip=22 mA when A/F=25. According to the diagram, it will be understood that it is sufficient to set as follows.

In case of −7 mA≦Ip≦7 mA (when A/F=12.8 to 18), the current detection resistance is set to "357 Ω" corresponding to the value of "R11+R12+R13".

In case of −11 mA≦Ip<−7 mA, 7 mA<Ip≦1.5 mA (when A/F=12 to 12.8, 18 to 22), the current detection resistance is set to "161 Ω" corresponding to the value of "R11+R12".

In case of 15.5 mA<Ip≦22 mA (when A/F=22 to 25), the current detection resistance is set to "113 Ω" corresponding to the value of "R11".

The operation of the air-fuel ratio detecting apparatus constructed as above will be explained.

Figure 12:
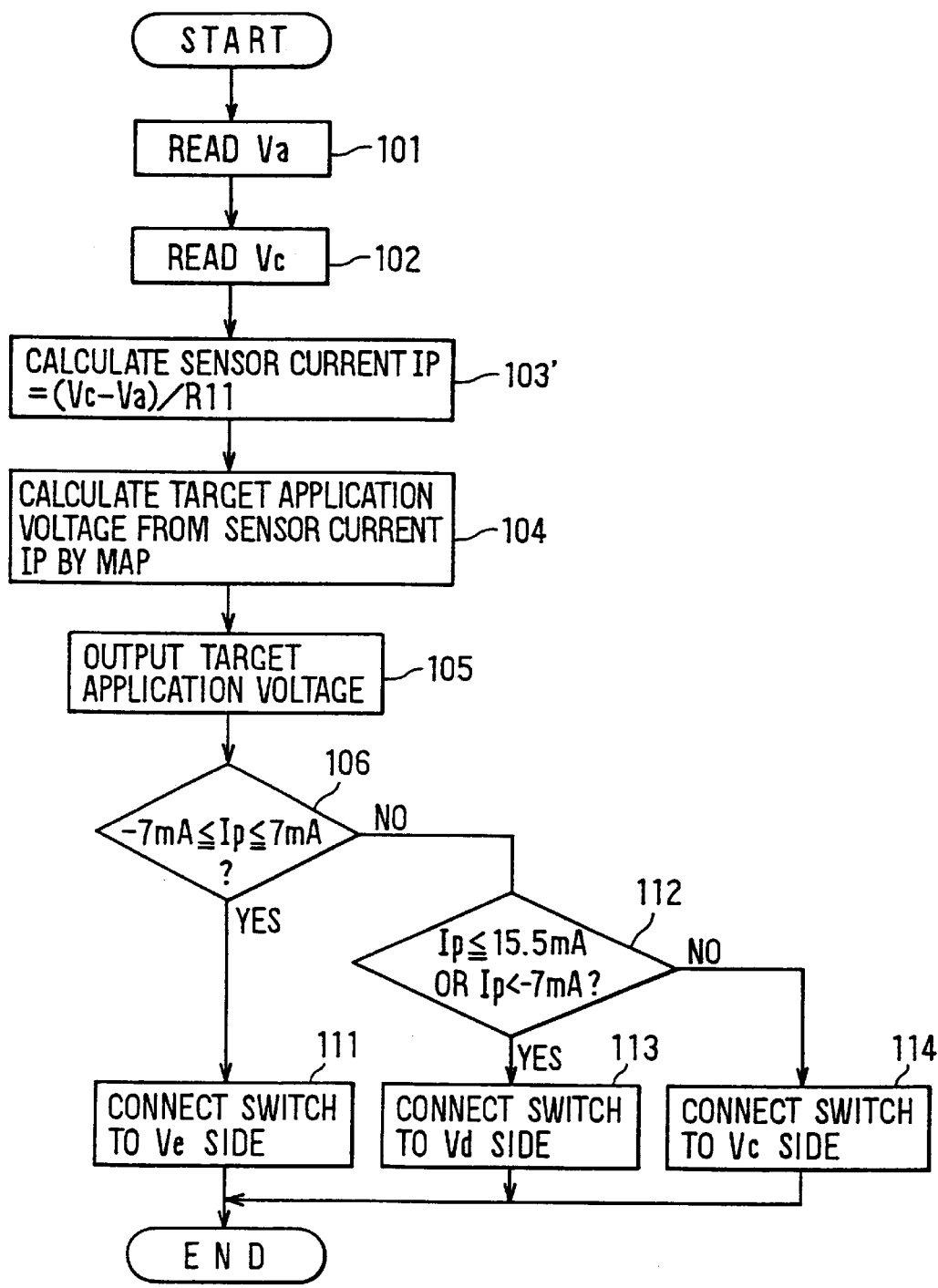
FIG. 12 is a flowchart showing an air-fuel ratio detecting routine in the second embodiment.

FIG. 12 is a flowchart showing an air-fuel ratio detecting routine executed by the CPU 21. The CPU 21 repeatedly executes this routine in a predetermined cycle (for example, an interval of 4 ms).

First, in steps 101 to 105, the CPU 21 detects the sensor current Ip which flows in accordance with the air-fuel ratio at each time in a manner similar to the routine of FIG. 6 and applies an application voltage corresponding to the sensor current Ip to the A/F sensor 30. In the embodiment, the sensor current Ip is calculated in step 103' from the arithmetic expression;

$$Ip=(Vc-Va)/R11$$

(where, R11 is a resistance value of the current detection resistor 15a).

Then, the CPU 21 discriminates whether the sensor current Ip at that time lies within a range of "−7 mA to 7 mA" or not in step 106. Ip=−7 mA and 7 mA are thresholds used to discriminate whether the air-fuel ratio at that time lies within the first air-fuel ratio zone (A/F=12.8 to 18) or not. When the step 106 is affirmatively discriminated, it denotes that the air-fuel ratio at that time lies within the first air-fuel ratio zone.

When the step 106 is affirmatively discriminated (in case of −7 mA≦Ip≦7 mA), the CPU 21 allows the switch circuit 52 to the voltage Ve side in step 111. Consequently, the input voltage Vf of the voltage follower 17 becomes the voltage Ve and the Ve value is outputted as an A/F output to the A/D converter 41 in the engine control ECU 40. The A/F output detected by the sensor current detection circuit 15 in this instance is detected by the sum "R11+R12+R13", of the resistance values of the current detection resistors 55a, 55b, and 15c.

When the step 106 is negatively discriminated, the CPU 21 discriminates whether the sensor current Ip at that time is within a range of "15.5 mA or smaller" or "less than −7 mA" in step 112. Ip=15.5 mA is a threshold used to discriminate whether the air-fuel ratio at that time lies within the second air-fuel ratio zone (A/F=18 to 22) or not. When the step 112 is affirmatively discriminated, it denotes that the air-fuel ratio at that time is within the second air-fuel ratio zone.

When the step 112 is affirmatively discriminated (in case of 7 mA<Ip≦15.5 mA or Ip<−7 mA), the CPU 21 allows the switch circuit 52 to be connected to the voltage Vd side in step 113. Consequently, the voltage Vd serves as the input voltage Vf of the voltage follower 17 and the Vd value is outputted as an A/F output to the A/D converter 41 in the engine control ECU 40. The A/F output detected by the sensor current detection circuit 15 is detected by the sum "R11+R12" of both of the resistance values of the current detection values 15a and 15b.

When the step 112 is negatively discriminated, the CPU 21 allows the switch circuit 52 to be connected to the voltage Vc side in step 114. Consequently, the voltage Vc serves as the input voltage Vf of the voltage follower 17 and the Vc value is outputted as an A/F output to the A/D converter 41 in the engine control ECU 40. In this instance, the A/F output detected by the sensor current detection circuit 15 is detected by the resistance value "R11" of the current detection resistor 15a.

According to the second embodiment as described above, in a manner similar to the first embodiment, the air-fuel ratio can be detected with high accuracy while limiting the output voltage of the air-fuel ratio detecting apparatus to the voltage range which is readable by the A/D converter 41. Therefore, effects such that the detection accuracy of the air-fuel ratio can be improved even when a wide air-fuel ratio detection zone is required can be obtained. As a result, also in the air-fuel ratio control system in which both of the stoichiometric control and lean-burn control are performed, while assuring detection accuracy of the air-fuel ratio at the time of lean-burn control, the detection accuracy of air-fuel ratio near the stoichiometric ratio can be improved.

Especially, in this embodiment, since the sensor current detection circuit 15 is constructed by the three current detection resistors 15a, 15b, and 15c, the air-fuel ratio detection with higher precision can be realized as compared with the first embodiment in which it is constructed by two current detection resistors. Since the resistance value is switched at the air-fuel ratio point (for instance, target air-fuel ratio) where the detection accuracy is required also in the embodiment, the air-fuel ratio detection as required can be realized.

In connection, four or more current detection resistors of the sensor current detection circuit may be provided and the air-fuel ratio zone for switching the resistance value can be further divided. In this case, the detection accuracy of the air-fuel ratio can be further improved.

(Third embodiment)

Figure 13:
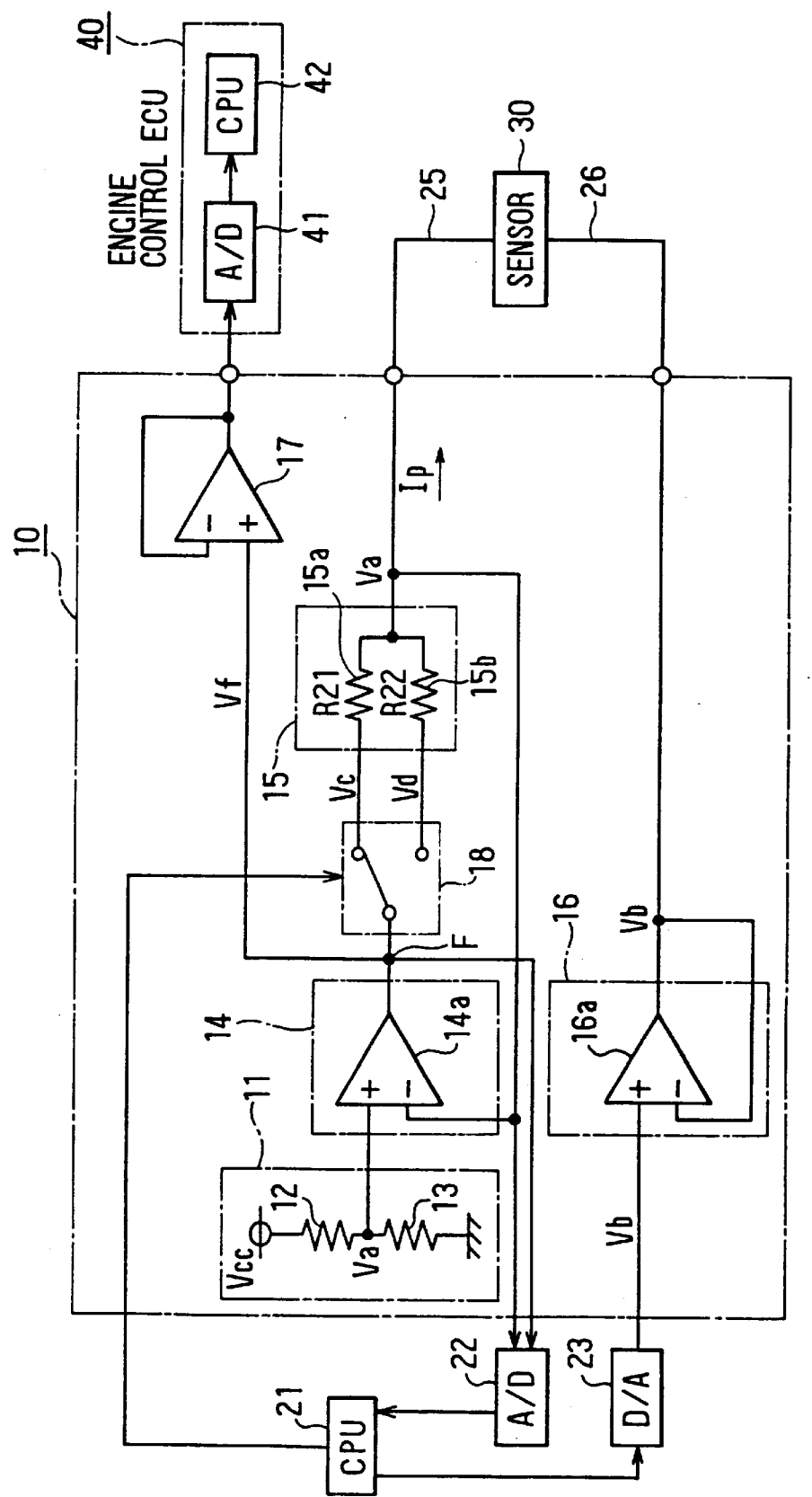
FIG. 13 is a circuit diagram showing an air-fuel ratio detecting apparatus according to a third embodiment.

The third embodiment of the invention will be described with reference to FIG. 13. FIG. 13 is a circuit diagram showing the outline of an air-fuel ratio detecting apparatus in the embodiment. The construction of the apparatus is basically similar to that of FIG. 1 of the first embodiment, so that only different points will be described hereinbelow.

According to the configuration of FIG. 13, a sensor current detection circuit 15 and a switch circuit 18 are serially connected between the output terminal of the amplifier 14a and the terminal 25 of the A/F sensor 30. The sensor current detection circuit 15 has two current detection resistors 15a and 15b which are connected in parallel. The point F between the output terminal of the amplifier 14a and the switch circuit 18 is connected to the non-inversion input terminal of the voltage follower 17 which receives the sensor current Ip as a voltage signal. The voltage Vf at the point F in the diagram is also received by the A/D converter 22.

In this case, when the switch circuit 18 is turned to the voltage Vc side as shown in the diagram, the voltage Vc serves as the voltage Vf of the input terminal of the voltage follower 17. That is, the sensor current Ip according to the air-fuel ratio is detected by the current detection resistor 15a and the voltage Vc corresponding to Ip is supplied to the voltage follower 17 via the point F in the diagram. When the switch circuit 18 is switched from the position shown in the diagram to the voltage Vd side, the voltage Vd serves as the voltage Vf of the input terminal of the voltage follower 17. That is, the sensor current Ip is detected by the current detection resistor 15b. The voltage Vd corresponding to Ip is supplied to the voltage follower 17 via the point F in the diagram.

The switching operation of the switch circuit 52 will be described by showing actual specific values. Methods of detecting the air-fuel ratio will be described with respect to the following two zones.

the zone near the stoichiometric ratio (A/F=12.8 to 18) in the dynamic range air-fuel ratio zones except for the zone near the stoichiometric ratio (A/F=12 to 12.8, 18 to 25)

In the embodiment, the reference voltage Va is set to "2.5V", the sensor current Ip when A/F=18 is set to "7 mA", and the sensor current Ip when A/F=25 is set to "22 mA" (V-I characteristic of FIG. 3). A resistance value R21 of the current detection resistor 15a is set to "113 Ω" and a resistance value R22 of the current detection resistor 15b is set to "357 Ω".

First, in the zone near the stoichiometric ratio (A/F=12.8 to 18), the air-fuel ratio at which the voltage Vc or the voltage vd is maximum is A/F=18 and the voltages Vc and vd when A/F=18 are as follows.

$Vc=3.291V$ $Vd=4.999V$

The voltage Vc is obtained by adding the reference voltage Va to the product of the sensor current Ip and the resistance value R21 of the current detection resistor 15a (Vc=Ip·R21+Va). The voltage Vd is obtained by adding the reference voltage Va to the product of the sensor current Ip and the resistance value R22 of the current detection resistor 15b (Vd=Ip·R22+Va).

Since both of the voltages Vc and Vd are within a voltage range (0 to 5V) which can be dealt by the A/D converter 41 in the engine control ECU 40, both of the values can be read by the A/D converter 41. As described above, in order to assure the detection accuracy, however, it is desirable to set the range of voltage value per unit A/F as large as possible. In this case, since the voltage Vd has the voltage value per unit A/F larger than the voltage Vc as described, it can be the that the voltage Vd has higher detection accuracy. There is a similar tendency for any A/F value if it is within the zone near the stoichiometric ratio (A/F=12.8 to 18). That is, the Vd value is used as the input voltage Vf of the voltage follower 17 in the zone near the stoichiometric ratio, the detection accuracy of the air-fuel ratio can be assured (FIGS. 4 and 5). It is sufficient that the value of the current detection resistor is "R22=357 Ω (value of the current detection resistor 15b).

On the other hand, the air-fuel ratio at which the voltage Vc or the voltage vd is maximum is A/F=25 in the air-fuel ratio zones (A/F=12 to 12.8, 18 to 25) other than the zone near the stoichiometric ratio. The voltages Vc and Vd when A/F=25 are as follows.

$Vc=4.986V$ $Vd=10.354V$

In this case, since the input voltage range of the A/D converter 41 is 0 to 5V, although the voltage Vc can be read, the voltage Vd cannot be read. In the air-fuel ratio zones (A/F=12 to 12.8, 18 to 25), therefore, the Vc value is used as the input voltage Vf of the voltage follower 17. That is, it is sufficient that the value of the current detection resistor is "R21=113 Ω" (value of the current detection resistor 15a).

In the air-fuel ratio detecting apparatus having the above configuration, an air-fuel ratio detecting process is performed basically according to the routine of FIG. 6 of the first embodiment (since the main construction is based on FIG. 6, a diagram is omitted here). When a point different from FIG. 6 is mentioned, the following equation is used to calculate the sensor current Ip (step 103 in FIG. 6) in the embodiment.

$Ip=(Vf-Va)/R21$ or $Ip=(Vf-Va)/R22$

That is, the sensor current Ip is calculated by using the potential difference between the voltage Vf and the voltage Va and the resistance value R21 (or R22) of the current detection resistor 15a (or 15b).

In the embodiment described above in detail, different from the first and second embodiments, the current detection resistors 15a and 15b in the sensor current detection circuit 15 are connected in parallel. In a manner similar to the above-mentioned embodiments, however, an effect such that the detection accuracy of the air-fuel ratio is improved even when a wide air-fuel ratio detection range is required is obtained. As a result, also in the air-fuel ratio control system in which both of the stoichiometric control and the lean-burn control are performed, the detection accuracy of the air-fuel ratio near the stoichiometric ratio can be improved while assuring the detection accuracy of the air-fuel ratio at the time of the lean burn control.

As another example of the third embodiment, it can be considered to embody the invention as follows. The sensor current detection circuit 15 has three or more current detection resistors which have different resistance values and are connected in parallel and the air-fuel ratio zone for switching the resistance value of the current detection resistor is further divided. In this case, the detection accuracy of the air-fuel ratio can be further improved.

(Fourth embodiment)

The fourth embodiment of the invention will be described with reference to FIG. 12. FIG. 12 is a circuit diagram showing the outline of an air-fuel ratio detecting apparatus in the embodiment. Since the construction of the apparatus is basically similar to that of FIG. 1 of the first embodiment, only different points will be described hereinbelow.

In the air-fuel ratio detecting apparatuses in the first to third embodiments, the switch circuit is arranged in the bias control circuit 10 and the CPU 21 variably sets the resistance value of the current detection resistor by switching the switch circuit in accordance with the sensor current Ip at each time. The detection accuracy of the air-fuel ratio is assured by the switching operation. On the contrary, in the apparatus of the present embodiment, the value of the current flowing in the A/F sensor 30 is outputted as a plurality of detection signals (A/F values) having different voltage levels. One of the plurality of detection signals to be used is selected in the engine control ECU 40 in accordance with the sensor current Ip.

Figure 14:
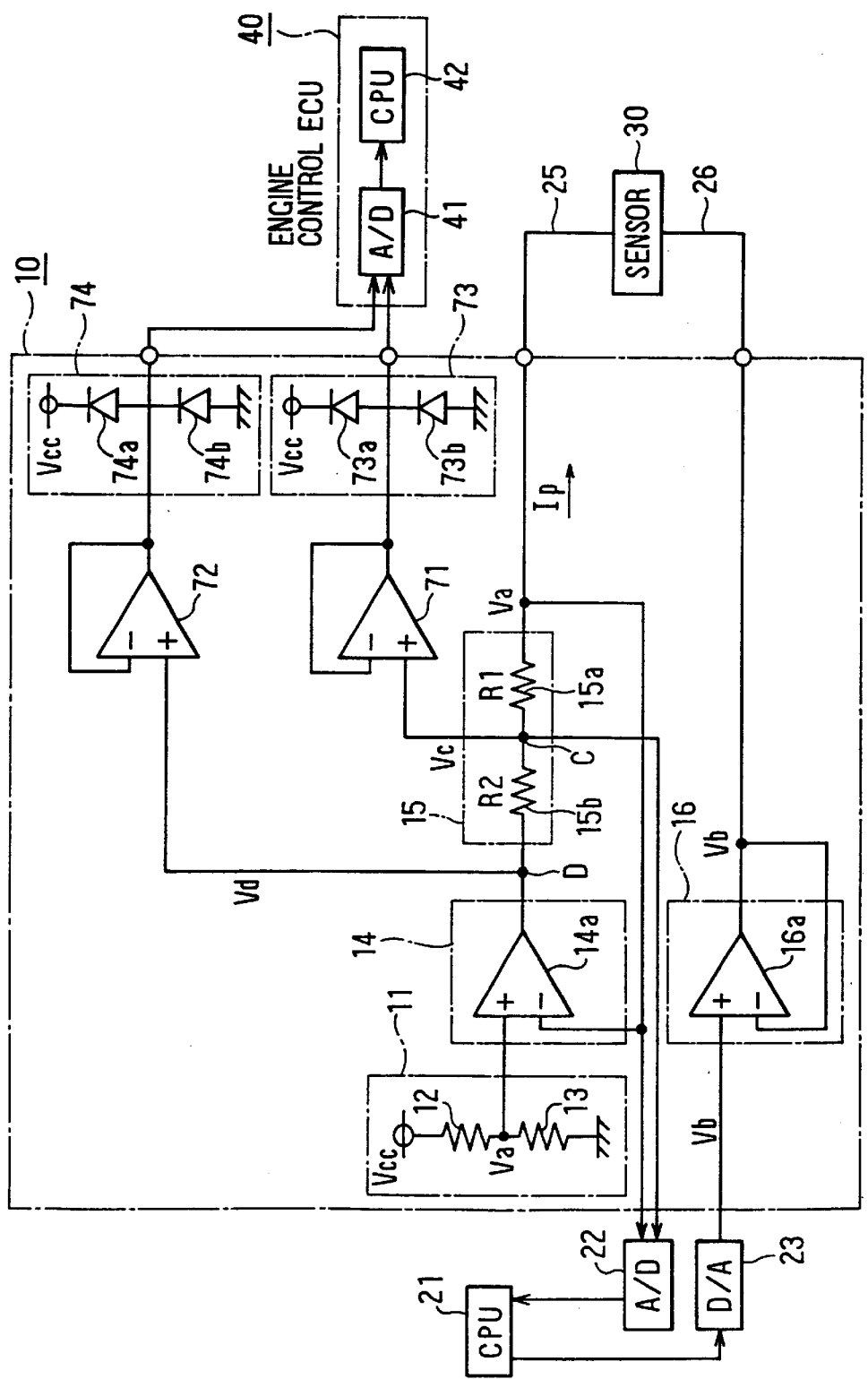
FIG. 14 is a circuit diagram showing an air-fuel ratio detecting apparatus according to a fourth embodiment.

In FIG. 14, the sensor current detection circuit 15 is provided between the output terminal of the amplifier 14a and the terminal 25 of the A/F sensor 30. Input terminals of voltage followers 71 and 72 are connected to the points C and D, respectively, between the output terminal of the amplifier 14a and the terminal 25 of the A/F sensor 30. The voltages Vc and Vd at the points C and D are applied to the voltage followers 71 and 72. The A/D converter 41 in the engine control ECU 40 is connected to the output terminals of the voltage followers 71 and 72 via clamp circuits 73 and 74 as voltage guarding means. The clamp circuit 73 comprises a pair of diodes 73a and 73b connected between the constant voltage Vcc and the ground. Similarly, the clamp circuit 74 comprises a pair of diodes 74a and 74b connected between the constant voltage Vcc and the ground. These clamp circuits 73 and 74 guard the outputs of the voltage followers 71 and 72 at the constant voltage Vcc.

According to the above configuration, different from the embodiments described, the switching operation of the switch circuit is unnecessary. The voltages Vc and Vd are applied to the engine control ECU 40 via the voltage followers 71 and 72. That is, the sensor current Ip flowing in the current detection resistors 15a and 15b is outputted as two A/F signals (voltages Vc and Vd). In a manner similar to the first embodiment, the resistance value R1 of the current detection resistor 15a is "113 W" and the resistance value R2 of the current detection resistor 15b is "244 Ω".

In this case, the engine control ECU 40 selects one of the two A/F signals in accordance with the air-fuel ratio (sensor current Ip) at each time. Specifically, when the sensor current Ip is "−7 mA to 7 mA", that is, when the air-fuel ratio at that time is within the zone near the stoichiometric ratio (A/F=12.8 to 18), the A/F value can be detected by the voltage Vd. When the sensor current Ip is "out of the range from −7 mA to 7 mA", that is, when the air-fuel ratio at that time is within the air-fuel ratio zones (A/F=12 to 12.8, 18 to 25) other than the zone near the stoichiometric ratio, the A/F value can be detected by the voltage Vc (characteristic diagram of FIG. 4 for details).

According to the fourth embodiment, in a manner similar to the foregoing embodiments, even when a wide air-fuel ratio detection range is required, the detection accuracy of the air-fuel ratio can be improved and the object of the invention can be achieved. In this case, the more the sensor current Ip is away from the stoichiometric ratio, a detection signal of an electric resistor having a low resistance value may be selected among the plurality of detection signals (Vc, Vd) (similar operation is performed when three or more current detection resistors are used).

In the embodiment, the clamp circuits 73 and 74 for regulating the output voltages of the voltage followers 71 and 72 so as to be in a predetermined voltage range which can be read by the A/D converter 41, that is, in the voltage range of 0 to 5V are provided. In this case, the output voltages of the voltage followers 71 and 72 become voltage signals which can be always read by the A/D converter 41, so that it can be prevented that an excess voltage is applied to the A/D converter 41. The invention can be also embodied by omitting the clamp circuits 71 and 72.

(Fifth Embodiment)

Next, the fifth embodiment will be described with reference to FIGS. 15 to 17. In this embodiment, when a resistance value of the sensor current detection circuit in the air-fuel ratio detecting apparatus is switched, the switching information is transmitted to an engine control ECU 40. Thus, even when the output voltages become the same against different air-fuel ratios, the engine control ECU 40 detects the air-fuel ratio accurately.

Figure 15:
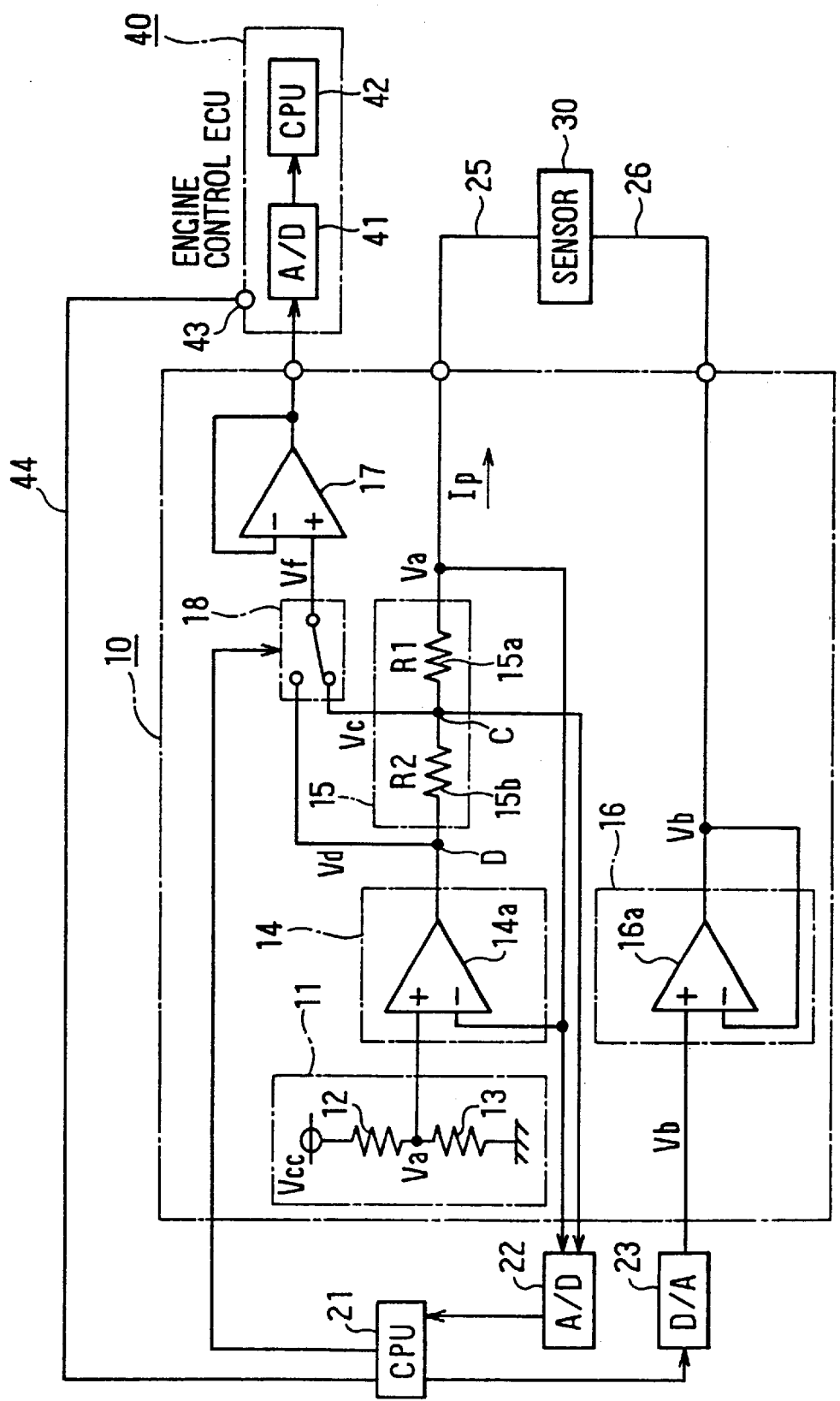
FIG. 15 is a circuit diagram showing an air-fuel ratio detecting apparatus according to a fifth embodiment.

FIG. 15 is a circuit diagram showing an outline of the air-fuel ratio detecting apparatus according to the present embodiment.

In FIG. 15, differeently from FIG. 1, the engine ECU 40 is provided with a digital port 43 which is connected to the CPU 21 through a signal line 44. The digital port 43 is held at either "0" or "1" in accordance with the range signal transmitted from the CPU 21.

Figure 16:
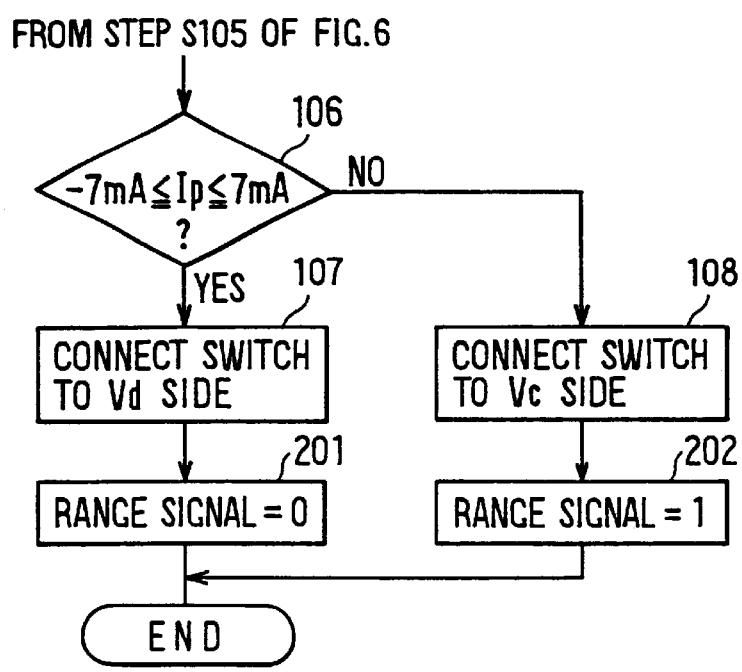
FIG. 16 is a flowchart showing a part of an air-fuel ratio detecting routine in the fifth embodiment.

FIG. 16 is a flowchart which shows a part of the air-fuel ratio detection routine executed by the CPU 21 and is a partial modification of the process shown in FIG. 6. In FIG. 16, the CPU 21 drives at steps 106 to 108 the switch circuit 18 in accordance with the sensor current Ip. That is, in the case of Ip=−7 mA to 7 mA, the CPU 21 drives the switch circuit 18 to the voltage Vd side (step 107) and, in the case of Ip<−7 mA or Ip>7 mA, drives the switch circuit 18 to the voltage Vc side (step 108).

When the switch circuit 18 is connected to the voltage Vd side, the CPU 21 clears the range signal to "0" at step 201. When the switch circuit 18 is connected to the voltage Vc side, the CPU 21 sets the range signal to "1" at step 202.

The engine control ECU 40 discriminates whether the range signal is "0" or "1" from the signal condition at the digital port 43. If the range signal is 0, the ECU 40 discriminates that the air-fuel ratio is detected in the range near the stoichiometric air-fuel ratio (A/F=12.8 to 18). If the range signal is 1, the ECU 40 discriminates that the air-fuel ratio is detected in the range other than the range near the stoichiometric air-fuel ratio.

Figure 17:
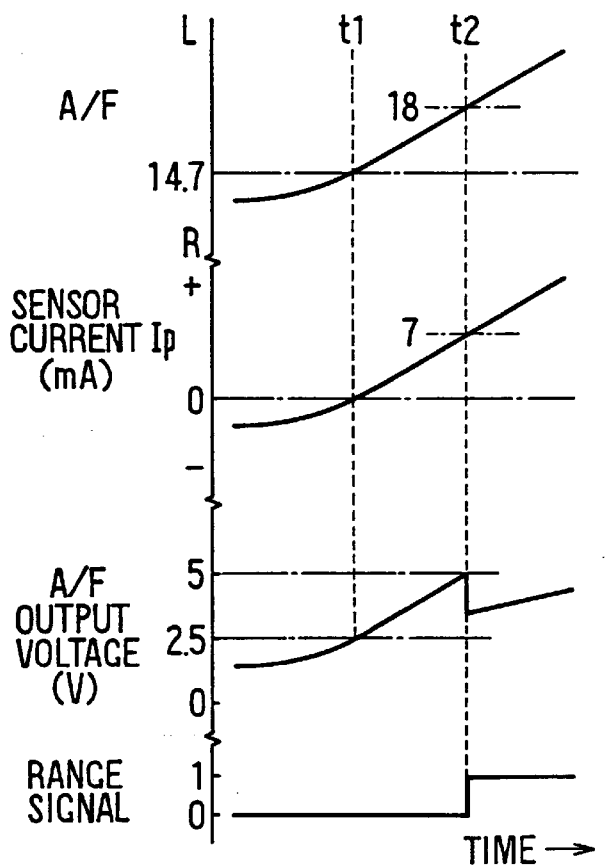
FIG. 17 is a time chart showing operation of the fifth embodiment.

FIG. 17 is a time chart showing in more detail the operation of the embodiment. In this figure, transitions of the sensor current Ip, A/F output voltage and range signal which occur when the air-fuel ratio changes from a rich value (for example, A/F=13) to a lean value (for example, A/F=25). It is assumed that the air-fuel ratio reaches the stoichiometric ratio at time t1 and reaches "18" at time t2.

Before time t2, the range signal is maintained at "0" because of Ip=−7 mA to 7 mA. As the sensor current Ip attains at time t2 "7 mA" which corresponds to A/F=18, the range signal is switched to "1". The engine control ECU 40 detects from the range signal that the switch circuit 18 is driven. Thus, even when the sensor output voltages are the same, two A/F values in the range near the stoichiometric ratio and in the other range.

According to the fifth embodiment, the engine control ECU 40 is enabled to determine accurately the air-fuel ratio (A/F value). As a result, the engine control ECU 40, thus determining the air-fuel ratio accurately, can perform a highly accurate air-fuel ratio control in response to the determined air-fuel ratio.

As a modification of the fifth embodiment, more than three current detection resistors may be switched over. In the case of switching three current detection resistors, for example, even when the sensor output voltages are the same, the engine control ECU 40 detects three A/F values for each air-fuel ratio range in response to the range signal.

(Sixth Embodiment)

Next, the sixth embodiment is described. In this embodiment, the engine control ECU 40 outputs a switching command to the switch circuit 18 and the CPU 21 performs switching operation of the switch circuit 18 in response to the command.

Figure 18:
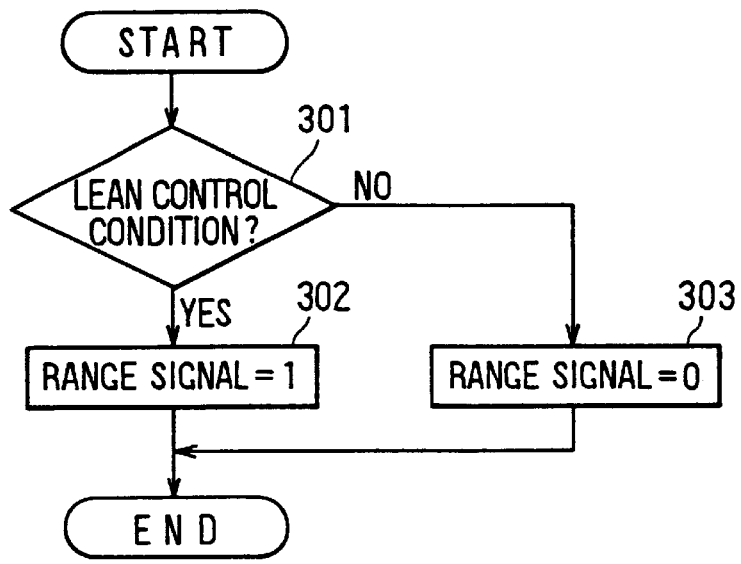
FIG. 18 is a flowchart showing a timer interrupt routine executed by an engine control ECU in a sixth embodiment.

FIG. 18 is a flowchart showing a timer interrupt routine executed by the engine control ECU 40. In FIG. 18, the engine control ECU 40 discriminates first at step 301 whether the lean control condition holds or not. The lean control condition includes, for examle:
the A/F sensor 30 is activated; and
the engine is in normal operation.

If the lean control condition holds, the engine control ECU 40 proceeds to step 302 to set the range signal to "1". If the lean control condition does not hold, the engine control ECU 40 proceeds to step 303 to set the range signal to "0".

Figure 19:
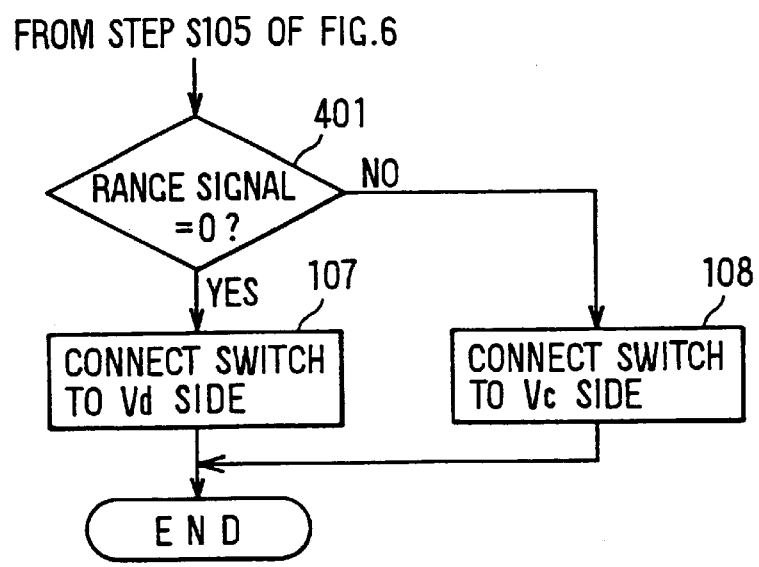
FIG. 19 is a flowchart showing a part of an air-fuel ratio detecting routine in the sixth embodiment.

The CPU 21 performs switching of the switch circuit 18 in response to the range signal set by the engine control ECU 40. That is, in the air-fuel ratio detection routine shown in FIG. 19, the CPU 21 discriminates at step 401 whether the range signal is "0" or not. If the range signal=0, the CPU 21 connects at step 107 the switch circuit 18 to the voltage Vd side. At this time, the air-fuel ratio near the stoichiometric ratio is detected. If the range signal=1, the CPU 21 connects at step 108 the switch circuit 18 to the voltage Vc side. At this time, the air-fuel ratio near the lean burn zone is detected. It is possible also in this embodiment to use more than three current detection resistors.

(Seventh Embodiment)

In this embodiment, the resistance value of the current detection resistor is set variably when sensor deteriortion is to be detected from a result of detecting atmospheric gas air-fuel ratio in the midst of the air-fuel ratio control. At the time of atmospheric gas air-fuel ratio detection, the air-fuel ratio becomes extreme lean and the sensor current IP becomes for example 136 mA". The resistance value of the current detection resistor is changed to "69 Ω" so that the air-fuel ratio may be detected within the signal processing range (0V to 5V) of the A/D converter 41 in the same manner as in the above embodiments. By setting the resistance value to 69 Ω, the input voltage Vf of the voltage follower 17 in FIG. 1, for instance, becomes:

$$Vf = 36 \text{ mA} \cdot 69 \text{ }\Omega + 2.5\text{V} = 4.984\text{V}$$

which is readable by the A/D converter 41. To be more specific, the engine control ECU 40 executes the processing in FIG. 20.

Figure 20:
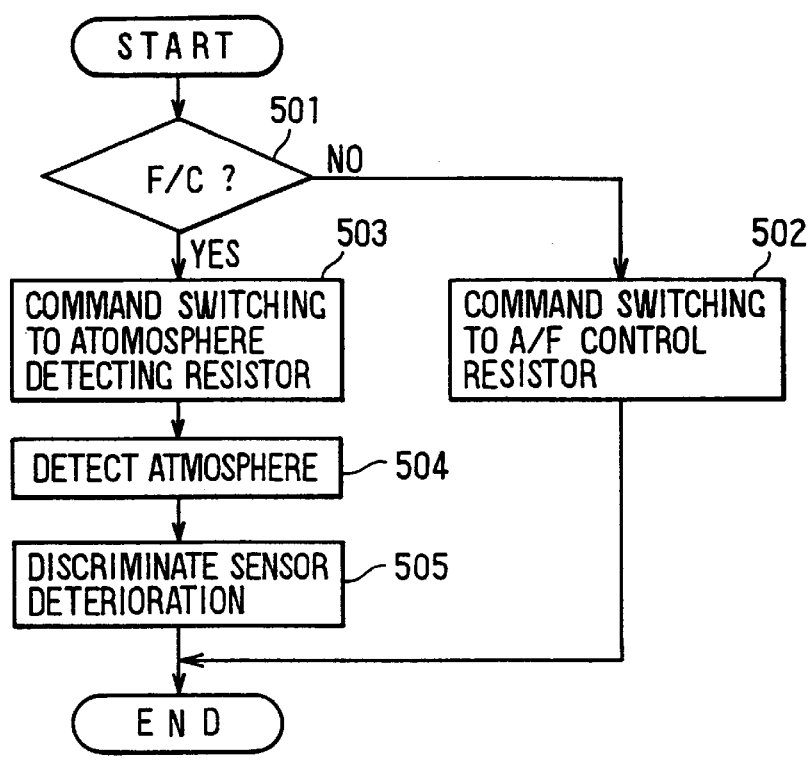
FIG. 20 is a flowchart showing a sensor deterioration discrimination processing in a seventh embodiment.

In FIG. 20, the engine control ECU 40 discriminates at step 501 whether it is in the fuel cut-off operation (F/C) at present or not. If NO, step 502 commands to CPU 21 an air-fuel ratio detection by the resistance value for the air-fuel ratio control. At this time, the CPU 21 performs switching of the switch circuit in response to the command from the engine control ECU 40.

If the discrimination at step 501 is YES, the engine contorol ECU 40 proceeds to step 503 to command to the CPU 21 an air-fuel ratio detection by the resistance value for the atmospheric gas air-fuel ratio detection. At this time, the CPU 21 performs switching of the switch circuit in response to the command from the engine control ECU 40. Then, the engine control ECU 40 detects the atmospheric gas air-fuel ratio at step 504 and discriminates deterioration of the A/F sensor 30 from the detected atmospheric air-fuel ratio at step 505. As an example, the sensor current Ip detected at step 504 is compared with a sensor current (predetermined threshold Ith) known at the time of atmospheric gas air-fuel ratio detection. If the Ip value and the Ith differ greatly, the sensor deterioration may be discriminated. If Ip<Ith, the sensor deterioration is discriminated as clogging in the electrodes of the A/F sensor 30 or small holes 31a of the cover 31 or as peeling-off of the electrodes.

As described above, the present invention may be applied even at the time of detecting the atmospheric gas air-fuel ratio detection. That is, the air-fuel ratio (sensor current Ip) can be detected accurately at either time of the air-fuel ratio control or the atmospheric gas air-fuel ratio control. Further, even at the time of detecting the atmospheric gas air-fuel ratio, no undesired influence will affect the air-fuel ratio feedback control operation.

Figure 21:
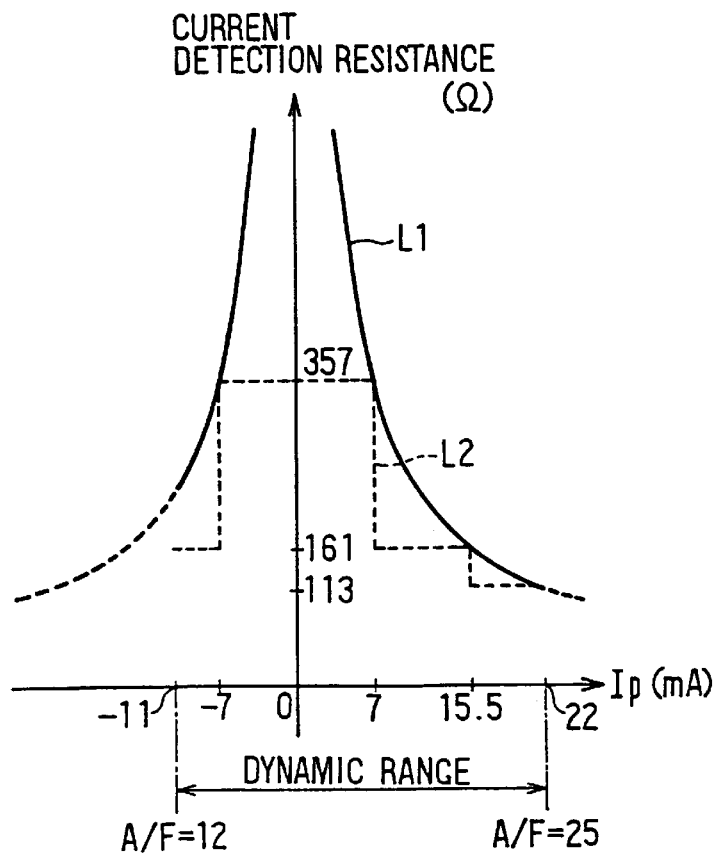
FIG. 21 is a graph showing the relation between the sensor current and the current detection resistor in the seventh embodiment.
Figure 22:
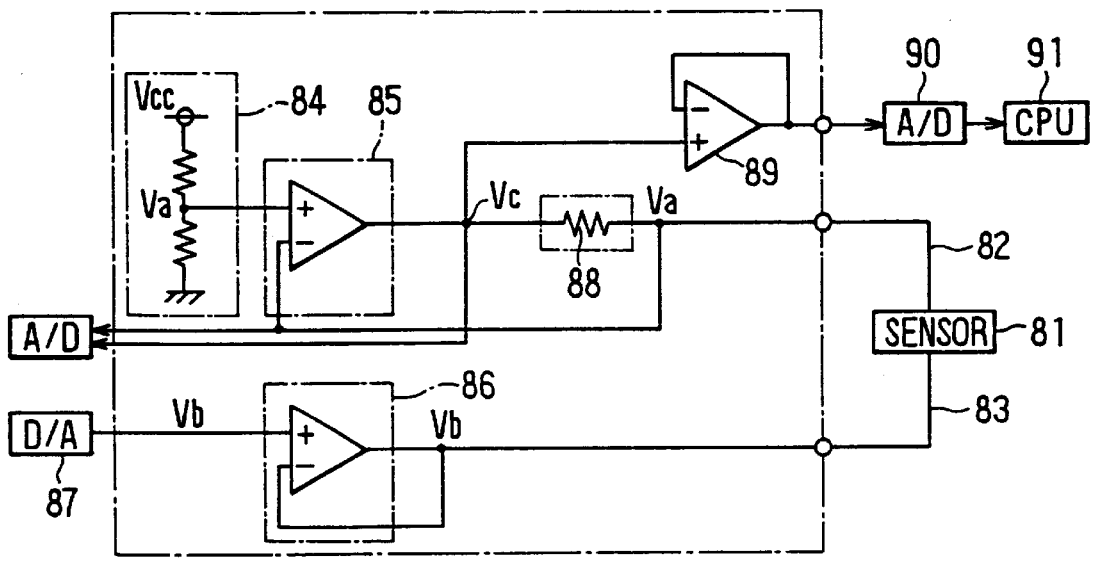
FIG. 22 is a circuit diagram showing a conventional air-fuel ratio detecting apparatus.
Figure 23:
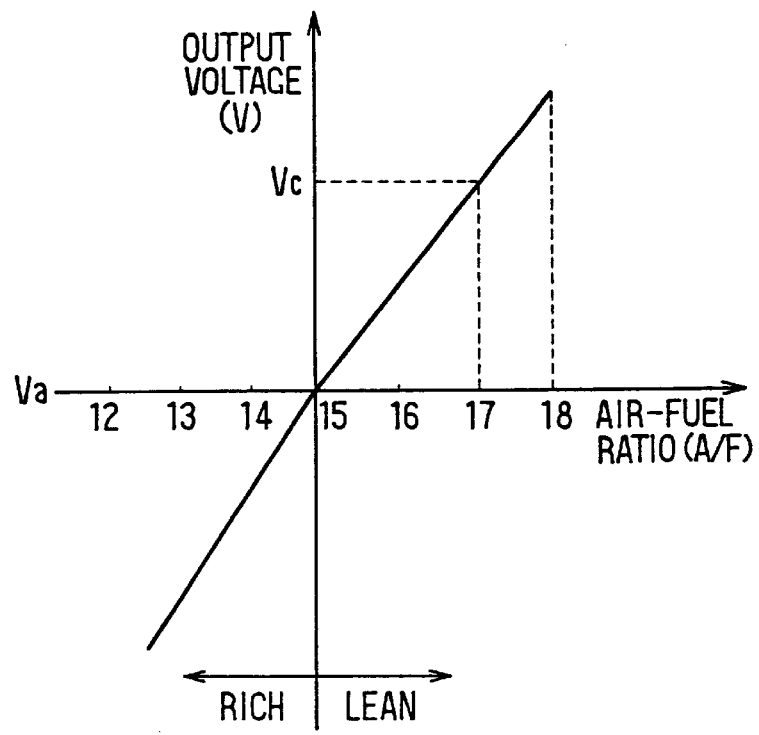
FIG. 23 is a graph showing an output voltage characteristic for each air-fuel ratio in the conventional apparatus.

As a current detection resistor of the sensor current detection circuit, a variable resistor whose resistance value can be optionally changed is used. In this case, as shown by a characteristic line L1 in FIG. 21, it is sufficient to change the resistance (Ω) of the current detection resistor in accordance with the sensor current Ip. In FIG. 21, a characteristic line L2 shown by a broken line is the same as the characteristic line shown in FIG. 11. When a plurality of current detection resistors are switched, it is sufficient to set the switching point on the characteristic line L1. Therefore, switching points of resistance values may be set arbitrarily on the line L1 in FIG. 21 other than the above-described resistance value switching points such as A/F=18 (Ip=7 mA) and A/F=22 (Ip=15.5 mA).

Although the reference voltage Va generated by the reference voltage circuit 11 is set to "2.5V" in the foregoing embodiments, the value may be changed. For example, in case of setting the reference voltage Va to a value smaller than "2.5V", the characteristic lines shown in FIGS. 5, 9, and 21 are shifted to the right side in the diagrams.

In recent years, an in-cylinder direct injection type engine in which fuel is injected directly into a cylinder (combustion chamber) of the engine is implemented. In the direct injection type engine, an air-fuel ratio control near an extreme lean zone (A/F=around 40) can be realized. In an air-fuel ratio control system in which the lean-burn control in the extreme lean zone is used, the dynamic range (air-fuel ratio detection range) is set to A/F=12 to 40 and the resistance value of the current detection resistor is variably set in the dynamic range. In the lean-burn control in the extreme lean zone, the target air-fuel ratio is set to, for example, A/F=around 37.

Specifically, when the reference voltage (FIG. 1) is set to "2.5V" and the sensor current Ip when A/F=40 is "28 mA", it is sufficient to set the resistance value of the current detection resistor to "89 Ω". That is, it is sufficient to use, for example, the voltage Vf of the non-inversion input terminal of the voltage follower 17 shown in FIG. 1 as a voltage value to be detected by the current detection resistor having the resistance value=89 Ω. In this case, the input voltage Vf of the voltage follower 17 is obtained by $$Vf=28\text{ mA}\cdot 89\text{ }\Omega+2.5V=4.992V,$$

which is a voltage value that can be read by the A/D converter 41. In a manner similar to, for instance, the first embodiment, therefore, when the air-fuel ratio point at which the current detection resistors are switched is set to, for example, A/F=12.8, 18 and in addition, A/F=25, it is sufficient that the resistance value of the current detection resistor is set to "357 Ω" when A/F=12.8 to 18, the resistance value of the current detection resistor is set to "113 Ω" when A/F=12 to 12.8, 18 to 25, and the resistance value of the current detection resistor is set to "89 Ω" when A/F=25 to 40.

The control in the extreme lean zone as mentioned above can be also applied to embodiments such as the fourth embodiment in which a plurality of voltage signals for respective air-fuel ratio zones are produced to the engine control ECU 40.

Further, although the switching of the switch circuit 18 is performed by the CPU 21 in the foregoing embodiments, it may be performed by the CPU 42 in the engine control ECU 40 in correspondence with required A/F accuracy.

Figure 8:
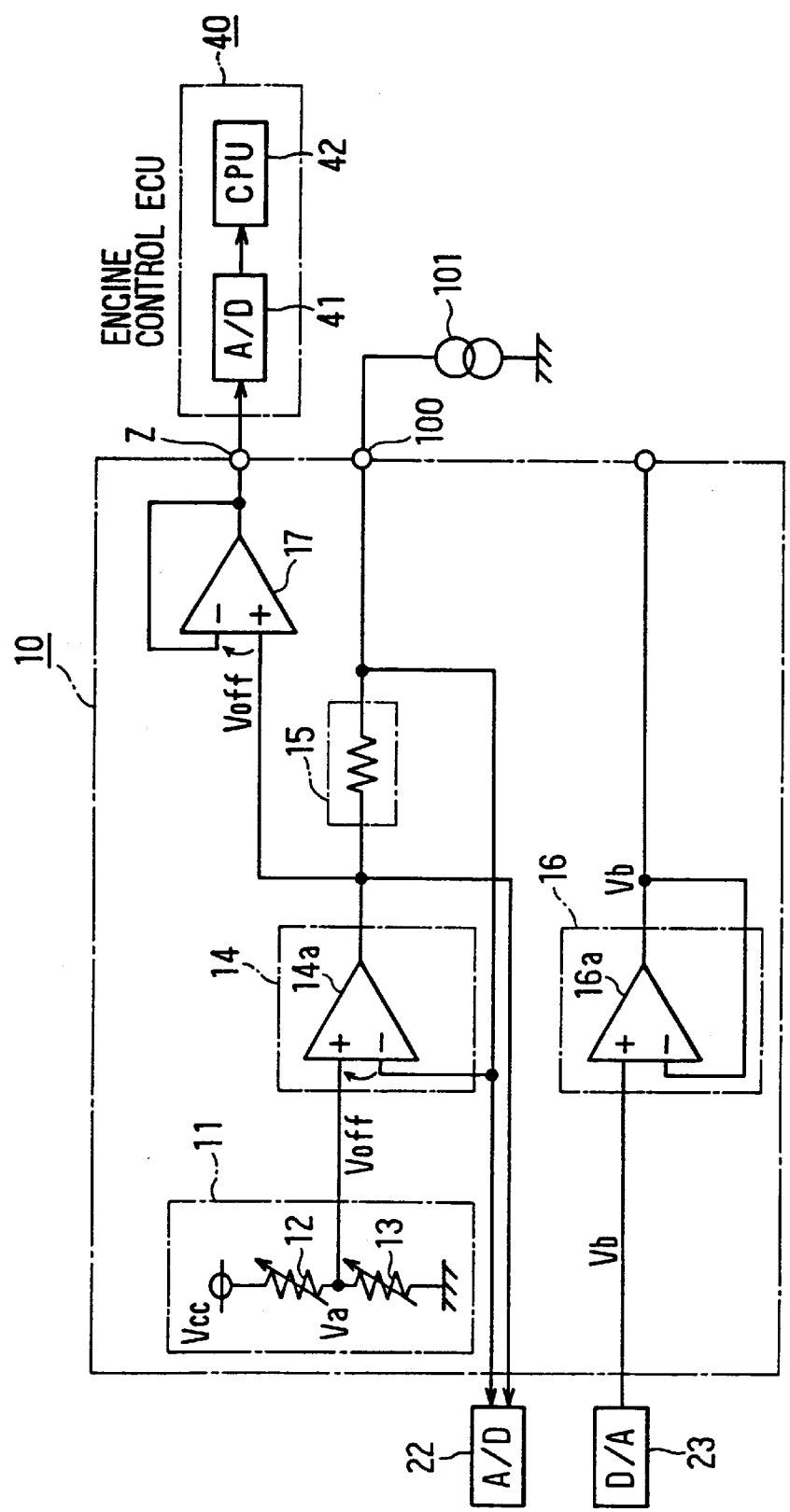
FIG. 8 is a circuit diagram showing an apparatus for adjusting the output voltage of the air-fuel ratio detecting apparatus.

Although the voltage value adjustment is performed based on the output voltage produced from the voltage follower 17 when the constant current (desired sensor current corresponding to the predetermined air-fuel ratio) is supplied by the constant current source 101 in FIG. 8 in the first embodiment, the output voltage may be adjusted by connecting the A/F sensor 30 to be used actually in place of the constant current source 101 in FIG. 8. In this instance, variations (variations among the devices) are reduced and the detection accuracy can be enhanced more.

Still further, the above output voltage adjustment (FIGS. 7 and 8) may be applied not only to the apparatus which sets variably the resistance value of the sensor current detection circuit but also to other air-fuel ratio detecting apparatus.

That is, it may be applied to air-fuel ratio detecting apparatuses which converts a sensor current to a voltage value, as long as the output voltage is adjusted by trimming voltage dividing resistors which produce a reference voltage. According to this output voltage adjustment, a highly accurate air-fuel ratio control apparatus can be provided even when a lean-burn system or direct injection engine is used or a more strict exhaust regulation is introduced in the furture.

Although the construction in which the voltage applied to the A/F sensor 30 is variably controlled by the bias control circuit 10 is used in the foregoing embodiments, the voltage applied to the A/F sensor 30 may be fixed. For example, in the construction shown in FIG. 1, the CPU 21, the A/D converter 22 and the D/A converter 23 are omitted and the switching operation of the switch circuit 18 is controlled by the engine control ECU 40.

Although the sensor current detection circuit is provided only on the terminal 25 side which is connected to the atmosphere side electrode layer 37 in the A/F sensor 30, this arrangement may be changed. For example, the sensor current detection circuit may be provided on the terminal 26 side connected to the outer atmosphere-gas side electrode layer 36 in the A/F sensor 30 or the sensor current detection circuits may be provided on both of the terminals 25 and 26. In short, it is sufficient as long as the sensor current detection circuit is provided in an electric path through which the sensor current Ip flows and the A/F signals at different voltage levels are obtained by the current detection resistor of the sensor current detection circuit.

Although the invention is embodied in the one-cell type limit current type air-fuel ratio sensor as the above embodiments, it may be changed. For example, the invention may be embodied in a two-cell type air-fuel ratio sensor. In the two-cell type air-fuel sensor, the air-fuel ratio is detected in accordance with a pumping current supplied to the sensor. Further, the invention may be embodied to a stack-type A/F sensor in place of the cup-shaped A/F sensor.

The present invention may be applied to apparatuses other than the air-fuel ratio detecting apparatus which uses the air-fuel ratio sensor. That is, the invention may be applied to a gas concentration detecting apparatus which uses a gas concentration sensor capable of detecting concentration of gas components such as NOx, HC, CO or the like.

What is claimed is:

1. A manufacturing method for manufacturing a current-generating type gas concentration detector circuit having its output coupled to an analog-to-digital converter working in a predetermined input signal range, said method of manufacturing comprising:

temporarily substituting into the circuit a constant current source for the gas concentration detector;

permanently adjusting a resistance of a reference voltage divider which provides a reference voltage normally applied to the gas detector to have a predetermined reference valve corresponding to the constant current source and magnitude; and removing said constant current source from the circuit and substituting the gas concentration detector back into said circuit for normal use thereafter in detecting gas concentrations.

2. A manufacturing method for manufacturing a gas concentration detecting apparatus including a gas concentration sensor for outputting a current signal corresponding to a gas concentration to be detected when a reference voltage is applied and which converts a current signal outputted from the sensor into a voltage signal output after A/D conversion to a signal processor which uses an A/D converted voltage signal in a predetermined voltage range, the method comprising the steps of:

connecting a constant current source in place of said gas concentration sensor;

monitoring the voltage signal;

adjusting the voltage signal by trimming at least one of a plurality of voltage dividing resistors which produce a reference voltage applied to the gas concentration sensor; and removing said constant current source from the circuit and substituting the gas concentration sensor into said apparatus for normal use thereafter in detecting gas concentrations.

3. A manufacturing method as in claim 2, further comprising the steps of:

converting the current signal of the gas concentration sensor by a resistor connected between the constant current source and an operational amplifier to which an output of the voltage dividing resistors is applied.

4. A manufacturing method as in claim 3, wherein a resistance of the at least one of the voltage dividing resistors is adjusted to fix the monitored voltage singal to a fixed value which is invariable with the current signal.

5. A manufacturing method for an engine condition detecting apparatus which includes a sensor for outputting a current signal corresponding to an engine condition to be detected when a bias voltage is applied, and a bias control circuit which applies the bias voltage to the sensor and converts the current signal outputted from the sensor into an output voltage signal, the method comprising the steps of:

connecting a constant current source to the bias control circuit in place of the gas concentration sensor to cause the bias control circuit to produce the output voltage signal in response to a constant current outputted from the constant current source;

monitoring the output voltage signal produced from the bias control circuit;

trimming a part of the bias control circuit until the monitored output voltage signal equals a fixed voltage signal predetermined in correspondence with the constant current; and removing said constant current source from the circuit and substituting the gas concentration sensor into said apparatus for normal use thereafter in detecting gas concentrations.

6. A manufacturing method as in claim 5, wherein:

the bias control circuit includes a reference voltage source for supplying a reference voltage, and a resistor connected between the reference voltage source and the constant current source to produce the output voltage signal; and the trimming step trims the reference voltage source.

7. A manufacturing method as in claim 6, wherein:

the sensor is a gas concentration responsive type for detecting a gas concentration of an engine;

the reference voltage source includes a plurality of resistors for supplying the reference voltage; and the trimming step trims a resistance of at least one of the resistors of the reference voltage source.

8. A manufacturing method as in claim 5, wherein the current signal is converted into the output voltage by a resistor which is connected to a source of the fixed voltage through an operational amplifier.

9. A manufacturing method as in claim 8, wherein the bias control circuit includes a resistor, and a resistance of the resistor is varied until the monitored output voltage signal equals the fixed voltage signal.

* * * * *

UNITED STATES PATENT AND TRADEMARK OFFICE
CERTIFICATE OF CORRECTION

PATENT NO. : 6,226,861 B1
DATED : May 8, 2001
INVENTOR(S) : Kurokawa et al.

Page 1 of 1

It is certified that error appears in the above-identified patent and that said Letters Patent is hereby corrected as shown below:

<u>Title page,</u>
Item [75] should read:

-- Inventors: Eiichi Kurokawa, Okazaki; Satoshi Hada, Kariya; Tomoo Kawase, Nagoya, Toshiyuki Suzuki, Handa; all of (JP) --

Signed and Sealed this

Thirteenth Day of November, 2001

Attest:

NICHOLAS P. GODICI
*Acting Director of the United States Patent and Trademark Office*

*Attesting Officer*